United States Patent
Van Nest

(10) Patent No.: US 7,157,437 B2
(45) Date of Patent: Jan. 2, 2007

(54) METHODS OF AMELIORATING SYMPTOMS OF HERPES INFECTION USING IMMUNOMODULATORY POLYNUCLEOTIDE SEQUENCES

(75) Inventor: Gary Van Nest, Martinez, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 09/802,518

(22) Filed: Mar. 9, 2001

(65) Prior Publication Data

US 2006/0264391 A1 Nov. 23, 2006

Related U.S. Application Data

(60) Provisional application No. 60/188,556, filed on Mar. 10, 2000.

(51) Int. Cl.
*A61K 48/00* (2006.01)
*C07H 21/02* (2006.01)
*C07H 21/04* (2006.01)

(52) U.S. Cl. .................................. 514/44; 536/23.1
(58) Field of Classification Search .............. 514/44
See application file for complete search history.

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,453,496 A | 9/1995 | Caruthers et al. | |
| 5,616,461 A | 4/1997 | Schafer et al. | |
| 5,663,153 A * | 9/1997 | Hutcherson et al. | 514/44 |
| 5,723,335 A | 3/1998 | Hutcherson et al. | |
| 5,849,719 A | 12/1998 | Carson et al. | |
| 5,874,089 A | 2/1999 | Schlegel et al. | |
| 6,174,872 B1 | 1/2001 | Carson et al. | |
| 6,218,371 B1 * | 4/2001 | Krieg et al. | 514/44 |
| 6,339,068 B1 | 1/2002 | Krieg et al. | |
| 6,406,705 B1 | 6/2002 | Davis et al. | |
| 6,498,148 B1 | 12/2002 | Raz | |
| 6,514,948 B1 | 2/2003 | Raz et al. | |
| 6,534,062 B1 | 3/2003 | Raz et al. | |
| 6,552,006 B1 | 4/2003 | Raz et al. | |
| 6,613,751 B1 | 9/2003 | Raz et al. | |
| 2001/0046967 A1 | 11/2001 | Van Nest | |
| 2002/0028784 A1 | 3/2002 | Nest | |
| 2002/0098199 A1 | 7/2002 | Van Nest et al. | |
| 2002/0107212 A1 | 8/2002 | Nest et al. | |
| 2003/0050263 A1 | 3/2003 | Krieg et al. | |
| 2003/0216340 A1 | 11/2003 | Van Nest et al. | |
| 2004/0009942 A1 | 1/2004 | Van Nest | |
| 2004/0030118 A1 | 2/2004 | Wagner et al. | 514/44 |
| 2005/0059626 A1 | 3/2005 | Van Nest et al. | |

FOREIGN PATENT DOCUMENTS

| | | |
|---|---|---|
| EP | 468520 A2 | 1/1992 |
| WO | WO 96/02555 A1 | 2/1996 |
| WO | WO 97/28259 A1 | 8/1997 |
| WO | WO 98/16247 A1 | 4/1998 |
| WO | WO 98/18810 A1 | 5/1998 |
| WO | WO 98/37919 A1 | 9/1998 |
| WO | WO 98/40100 A1 | 9/1998 |
| WO | WO 98/52581 A1 | 11/1998 |
| WO | WO 98/52962 A1 | 11/1998 |
| WO | WO 98/55495 A2 | 12/1998 |
| WO | WO 98/55495 A3 | 12/1998 |
| WO | WO 98/55609 A1 | 12/1998 |
| WO | WO 99/11275 A2 | 3/1999 |
| WO | WO 99/11275 A3 | 3/1999 |
| WO | WO 99/33488 A2 | 7/1999 |
| WO | WO 99/33488 A3 | 7/1999 |
| WO | WO 99/33868 A2 | 7/1999 |
| WO | WO 99/33868 A3 | 7/1999 |
| WO | WO 99/51259 A2 | 10/1999 |
| WO | WO 99/51259 A3 | 10/1999 |
| WO | WO 99/56755 A1 | 11/1999 |
| WO | WO 99/62923 A2 | 12/1999 |
| WO | WO 99/62923 A3 | 12/1999 |
| WO | WO 00/06588 A1 | 2/2000 |
| WO | WO 00/16804 A1 | 3/2000 |

(Continued)

OTHER PUBLICATIONS

Tokunaga et al., How BCG led to the discovery of immunostimulatory DNA, 1999, Jpn. J. Infect. Dis., vol. 52, pp. 1-11.*

(Continued)

*Primary Examiner*—Daniel M. Sullivan
(74) *Attorney, Agent, or Firm*—Morrison & Foerster LLP

(57) ABSTRACT

The invention provides new methods of preventing and/or treating herpes virus infections, particularly reducing infection, one or more symptoms and recurrence of one or more symptoms of herpes simplex virus infection. A polynucleotide comprising an immunostimulatory sequence (an "ISS") is administered to an individual which is at risk of being posed to alphaherpesvirinae, has been exposed to alphaherpesvirinae or is infected with alphaherpesvirinae. The ISS is administered without any alphaherpesvirinae antigens. Administration of the ISS results in reduced incidence, recurrence, and severity of one or more symptoms of alphaherpesvirinae infection.

23 Claims, 4 Drawing Sheets

FOREIGN PATENT DOCUMENTS

| | | |
|---|---|---|
| WO | WO 00/21556 A1 | 4/2000 |
| WO | WO 00/62802 A2 | 10/2000 |
| WO | WO 00/62802 A3 | 10/2000 |
| WO | WO 00/67023 A1 | 11/2000 |
| WO | WO 01/02007 A1 | 1/2001 |
| WO | WO 01/12223 A2 | 2/2001 |
| WO | WO 01/55341 A2 | 8/2001 |
| WO | WO 01/55341 A3 | 8/2001 |
| WO | WO 01/68077 A2 | 9/2001 |
| WO | WO 01/68077 A3 | 9/2001 |
| WO | WO 01/68078 A2 | 9/2001 |
| WO | WO 01/68078 A3 | 9/2001 |
| WO | WO-01/68103 A2 | 9/2001 |
| WO | WO-01/68103 A3 | 9/2001 |
| WO | WO 01/68116 A2 | 9/2001 |
| WO | WO 01/68116 A3 | 9/2001 |
| WO | WO 01/68117 A2 | 9/2001 |
| WO | WO 01/68117 A3 | 9/2001 |
| WO | WO 01/68143 A2 | 9/2001 |
| WO | WO 01/68143 A3 | 9/2001 |
| WO | WO 01/68144 A2 | 9/2001 |
| WO | WO 01/68144 A3 | 9/2001 |
| WO | WO 01/76642 A1 | 10/2001 |

OTHER PUBLICATIONS

Krieg, Direct immunologic activities of CpG DNA and implications for gene therapy, 1999, The Journal of Gene Medicine, vol. 1, pp. 56-63.*

Verma et al., Gene therapy-promises, problems and prospects, 1997, NATURE, vol. 389, pp. 239-242.*

Marshall, Gene therapy's growing pains, 1995, SCIENCE, vol. 269, pp. 1050-1055.*

Orkin et al., Report and recommendations of the panel to assess the NIH investment in research on gene therapy, 1995, NIH.*

Mountain, Gene therapy: the first decade, 2000, TIBTECH, vol. 18, pp. 119-128.*

Kmiec, Gene therapy, 1999,American Scientist, vol. 87, pp. 240-247.*

Weiner et al. Immunostimulatory oligodeoxynucleotides containing the CpG motif are effective as immune adjuvants in tumor antigen immunization. Proc Natl Acad Sci U S A. Sep. 30, 1997;94(20):10833-7.*

Hartmann et al. Delineation of a CpG phosphorothioate oligodeoxynucleotide for activating primate immune responses in vitro and in vivo. J Immunol. Feb. 1, 2000;164(3):1617-24.*

Pyles et al. Use of immunostimulatory sequence-containing oligonucleotides as topical therapy for genital herpes simplex virus type 2 infection. nJ Virol. Nov. 2002;76(22):11387-96.*

Rosenthal et al. Seroprevalence of herpes simplex virus types 1 and 2 and cytomegalovirus in adolescents. Clin Infect Dis. Feb. 1997;24(2):135-9.*

Ausubel, Fredrick M. et al., eds. (1995). *Current Protocols in Molecular Biology*. vol. 1, John Wiley & Sons, Inc.: pp. iii-xii (Table of Contents).

Ballus, Zuhair et al. (1996). "Induction of NK Activity in Murine and Human Cells by CpG Motifs in Oligodeoxynucleotides and Bacterial DNA" *J. Immunol.* 157:1840-1845.

Beaucage, Sarge L. (1993). "Oligodeoxyribonucleotide Synthesis" vol. 20 Chapter 2 in *Protocols for Oligonucleotides and Analogs, Synthesis and Properties*, Agrawal (ed.), Humana Press: Totowa, NJ. pp. 33-61.

Bourne, Nigel et al. (1996). "DNA Immunization Against Experimental Genital Herpes Simplex Virus Infection" *J. Infest. Dis.* 173(4):800-807.

Bourne, Nigel et al. (1996). "DNA Immunization Confers Protective Immunity on Mice Challenged Intravaginally with Herpes Simplex Virus Type 2" *Vaccine* 14(13):1230-1234.

Branda, Richard F. et al. (1993). "Immune Stimulation by an Antisense Oligomer Complementary to the Rev Gene of HIV-1" *Biochem. Pharmacol.* 45(10):2037-2043.

Branda, Richard F. et al. (1996). "Amplification of Antibody Production by Phosphorothioate Oligodeoxynucleotides" *J. Lab. Clin. Med.* 128(3):329-338.

Braun, Ralph P. and Lee, Jeremy S. (1998). "Immunogenic Duplex Nucleic Acids are Nuclease Resistant" J. Immunol. 141(6):2084-2089.

Brazolot Millan, Cynthia L. et al. (1998). "CpG DNA can Induce Strong Th1 Humoral and Cell-Mediated Immune Responses Against Hepatitis B Surface Antigen in Young Mice" *Proc. Natl. Acad. Sci. USA* 95:15553-15558.

Broide, David et al. (1998). "Immunostimulatory DNA Sequences Inhibit IL-5, Eosinophilic Inflammation, and Airway Hyperresponsiveness in Mice" *J. Immunol.* 161:7054-7062.

Broide, David and Raz, Eyal (1999). "DNA-Based Immunization for Asthma" *Int. Arch. Allergy Immunol.* 118:453-456.

Burke, Rae Lyn et al. (1994). "Influence of Adjuvant on the Therapeutic Efficacy of a Recombinant Genital Herpes Vaccine" *J. Infect. Dis.* 170:1110-1119.

Carson, Dennis A. and Raz, Eyal (1997). "Oligonucleotide Adjuvants for T Helper 1 (Th1)-Specific Vaccination" *J. Exp. Med.* 186(10):1621-1622.

Chace, Jacqueline H. et al. (1997). "Bacterial DNA-Induced NK Cell IFN-Gamma Production is Dependent on Macrophage Secretion of IL-12" *Clin. Immunol. and Immunopathol.* 84(2):185-193.

Chaturvedi, Surendra et al. (1996). "Stabilization of Triple-Stranded Oligonucleotide Complexes: Use of Probes Containing Alternating Phosphodiester and Stereo-Uniform Cationic Phosphoramidate Linkages" *Nucleic Acids Res.* 24(12):2318-2323.

Chu, Rose S. et al. (1997). "CpG Oligodeoxynucleotides Act as Adjuvants that Switch on T Helper 1 (Th1) Immunity" *J. Exp. Med.* 186(10):1623-1631.

Clements, John D. (1997). "Surface Warfare Against Pathogens Using Mucosal Vaccines" *Nature Biotech.* 15:622-623.

Coligan, John E. et al., eds. (1998). *Current Protocols in Immunology* vol. 1, John Wiley & Sons, Inc: pp. 1-9 (Table of Contents).

Cowdery, John S. et al. (1996). "Bacterial DNA Induces NK Cells to Produce IFN-Gamma in Vivo and Increases the Toxicity of Lipopolysaccharides" *J. Immunol.* 156:4570-4575.

Damhoff, R.A. et al. (1994). "Purification of the Integral Membrane Glycoproteins D of Herpes Simplex Virus Type 1 and 2, Produced in the Recombinant Baculovirus Expression System, by Ion-Exchange High-Performance Liquid Chromatography" *J. Chromatogr. A* 676:43-49.

Elkins, Karen L. et al. (1999). "Bacterial DNA Containing CpG Motifs Stimulates Lymphoctyes-Dependent Protection of Mice Against Lethal Infection with Intracellular Bacteria" *J. Immunol.* 162:2291-2298.

Freshney, R.I., ed. (1987). *Animal Cell Culture: A Practical Approach*. IRL Press: pp. vii-xii (Table of Contents).

Gait, M. J., ed. (1984). *Oligonucleotide Synthesis: A Practical Approach* IRL Press: pp. vii-xii (Table of Contents).

Gao, Hetian et al. (1995). "Circulation of Oligonucleotides by Disulfide Bridge Formation" *Nucleic Acids Res.* 23(11):2025-2029.

Godard, Gérard et al. (1995). "Antisense Effects of Cholesterol-Oligodeoxynucleotide Conjugates Associated with Poly(Alkylcyanoacrylate) Nanoparticles" *Eur. J. Biochem.* 232:404-410.

Gramzinski, Robert A. et al. (1998). "Immune Response to a Hepatitis B DNA Vaccine in Aotus Monkeys: a Comparison of Vaccine Formulation, Route, and Method of Administration" *Mol. Med.* 4:109-118.

Horner, Anthony A. et al. (1998). "Immunostimulatory DNA is a Potent Mucosal Adjuvant" *Cell. Immunol.* 190:77-82.

Jäger, Alfred et al. (1988). "Oligonucleotide N-Alkylphosphoramidates: Synthesis and Binding to Polynucleotides" *Biochem.* 27(19):7237-7246.

Jakob, Thilo et al. (1998). "Activation of Cutaneous Dendritic Cells by CpG-Containing Oligodeoxynucleotides: a Role for Dendritic Cells in the Augmentation of Th1 Responses by Immunostimulatory DNA" *J. Immunol.* 161:3042-3049.

Johannsson, Eva-Liz et al. (1998). "Antibodies and Antibody-Secreting Cells in the Female Genital Tract After Vaginal or Intranasal Immunization with Colera Toxin B Subunit or Conjugates" *Inf. Immun.* 66(2):514-520.

Kataoka, Tetsuro et al. (1992). "Antitumor Activity of Synthetic Oligonucleotides with Sequences from cDNA Encoding Proteins of *Mycobacterium bovis* BCG" *Jpn. J. Cancer Res.* 83:244-247.

Kimura, Yoshimitsu et al. (1994). "Binding of Oligoguanylate to Scavenger Receptors is Required for Oligonucleotides to Augment NK Cell Activity and Induce IFN" *J. Biochem.* (Tokyo) 116(5):991-994.

Kinghorn, George R. (1996). "Limiting the Spread of Genital Herpes" *Scand. J. Infect. Dis. Suppl.* 100:20-25.

Kline, J. N. et al. (1997). "Immune Redirection by CpG Oligonucleotides Conversion of a Th2 Response to a Th1 Response in a Murine Model of Asthma" *J. Invest. Med.* 45(3):282A.

Klinman, Dennis M. et al. (1996). "CpG Motifs Present in Bacterial DNA Rapidly Induce Lymphocytes to Secrete Interleukin 6, Interleukin 12, and Interferon Gamma" *Proc. Natl. Acad. Sci. USA* 93:2879-2883.

Klinman, Dennis M. et al. (1997). "Contribution of CpG Motifs to the Immunogenicity of DNA Vaccines" *J. Immunol.* 158:3635-3639.

Kovarik, Jiri et al. (1999). "CpG Oligodeoxynucleotides can Circumvent the Th2 Polarization of Neonatal Responses to Vaccines but May Fail to Fully Redirect Th2 Responses Established by Neonatal Priming" *J. Immunol.* 162:1611-1617.

Krieg, Arthur M. et al. (1989). "A Role for Endogenous Retroviral Sequences in the Regulation of Lymphocyte Activation" *J. Immunol.* 143(8):2448-2451.

Krieg, Arthur M. et al. (1995). "CpG Motifs in Bacterial DNA Trigger Direct B-Cell Activation" *Nature* 374:546-549.

Krieg, Arthur M. (1996). "Lymphocyte Activation by CpG Dinucleotide Motifs in Prokaryotic DNA" *Trends Microbiol.* 4(2):73-77.

Krieg, Arthur M. et al. (1996). "Oligodeoxynucleotide Modifications Determine the Magnitude of B Cell Stimulation by CpG Motifs" *Antisense Nucleic Acid Drug Dev.* 6:133-139.

Krieg, Arthur M. (1998). "Leukocyte Stimulation by Oligodeoxynucleotides" Chapter 24 in *Applied Antisense Oligonucleotide Technology* C.A. Stein et al. eds. Wiley-Liss, Inc.: pp. 431-448.

Krieg, Arthur M. et al. (1998a). "The Role of CpG Dinucleotides in DNA Vaccines" *Trends Microbiol.* 6(1):23-27.

Krieg, Arthur M. et al. (1998b). "CpG DNA Induces Sustained IL-12 Expression in Vivo and Resistance to Listeria Monocytogenes Challenge" *J. Immunol.* 161:2428-2434.

Krieg, Arthur M. et al. (1998c). "Sequence Motifs in Adenoviral DNA Block Immune Activation by Stimulatory CpG Motifs" *Proc. Natl. Acad. Sci. USA* 95:12631-12636.

Krieg, Arthur M. (1999). "CpG DNA: a Novel Immunomodulator" *Trends Microbiol.* 7(2):64-65.

Langenberg, Andria G.M. (1995). "A Recombinant Glycoprotein Vaccine for Herpes Simplex Type 2: Safety and Efficacy" *Ann. Intern. Med.* 122(12):889-898.

Latimer, Laura J. P. et al. (1995). "Specificity of Monoclonal Antibodies Produced Against Phosphorothioate and Ribo Modified DNAs" *Mol. Immunol.* 32(14/15):1057-1064.

Leclerc, Claude et al. (1997). "The Preferential Induction of a Th1 Immune Response by DNA-Based Immunization in Mediated by the Immunostimulatory Effect of Plasmid DNA" *Cell Immunol.* 179:97-106.

Liang, Hua et al. (1996). "Activation of Human B Cells by Phosphorothioate Oligodeoxynucleotides" *J. Clin. Invest.* 98(5):1119-1129.

Lipford, Grayson B. et al. (1997a). "CpG-Containing Synthetic Oligonucleotides Promote B and Cytotoxic T Cell Responses to Protein Antigen: A New Class of Vaccine Adjuvants" *Eur. J. Immunol.* 27:2340-2344.

Lipford, Grayson B. et al. (1997b). "Immunostimulatory DNA: Sequence-Dependent Production of Potentially Harmful or Useful Cytokines" *Eur. J. Immunol.* 27:3420-3426.

Liu, Hsin-Ming et al. (1998). "Immunostimulatory CpG Oligodeoxynucleotides Enhance the Immune Response to Vaccine Strategies Involving Granulocyte-Macrophage Colony-Stimulating Factor" *Blood* 92(10):3730-3736.

Macfarlane, D.E. et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step" *Immunology* 91:586-593.

Manzel, Lori and MacFarlane, Donald E. (1999). "Lack of Immune Stimulation by Immobilized CpG-Oligodeoxynucleotide" *Antisense Nucl. Acid Drug Dev.* 9:459-464.

Martin-Orozco, Elena et al. (1999). "Enhancement of Antigen-Presenting Cell Surface Molecules Involved in Cognate Interactions by Immunostimulatory DNA Sequences" *Int. Immunol.* 11(7):1111-1118.

Masseyeff, René F., ed. (1993). *Methods of Immunological Analysis. vol. 1: Fundamentals.* Verlagsgesellschaft mbH, D-6940: Weinheim, Germany: pp. xi-xxii (Table of Contents).

Matteucci (1997) "Oligonucleotide Analogs:an Overview" in *Oligonucleotides as Therapeutic Agents*, (D.J. Chadwick and G. Cardew, ed.) John Wiley and Sons, New York, NY: pp. 5-18.

McCluskie, Michael J. and Davis, Heather L. (1998). "CpG DNA is a Potent Enhancer of Systemic and Mucosal Immune Responses Against Hepatitis B Surface Antigen with Intranasal Administration to Mice" *J. Immunol.* 161:4463-4466.

McDermott, Mark R. et al. (1970). "Mucosal and Systemic Antiviral Antibodies in Mice Inoculated Intravaginally with Herpes Simplex Virus Type 2" *J. Gen. Virol.* 71:1497-1504.

Miller, Jeffrey H. and Calos, Michele B., eds. (1987). "Gene Transfer Vectors for Mammalian Cells" *in Current Communications in Molecular Biology.* Cold Spring Harbor Laboratory: pp. vii-ix (Table of Contents).

Miller, Paul S. et al. (1971). "Syntheses and Properties and Adenine and Thymine Nucleoside Alkyl Phosphotriesters, the Neutral Analogs of Dinucleoside Monophosphates" *JACS* 93(24):6657-6665.

Milligan, Gregg N. and Bernstein, David I. (1995). "Generation of Humoral Immune Responses Against Herpes Simplex Virus Type 2 in the Murine Female Genital Tract" *Virol.* 206:234-241.

Mojcik, Christopher F. et al. (1993). "Administration of a Phosphorothioate Oligonucleotide Antisense to Murine Endogenous Retroviral MCF *Env* Causes Immune Effects *in Vivo* in a Sequence-Specific Manner" *Clin. Immunol. and Immunopathol.* 67(2):130-136.

Moldoveanu, Zina et al. (1998). "CpG DNA, a Novel Immune Enhancer for Systemic and Mucosal Immunization with Influenza Virus" *Vaccine* 16(11/12):1216-1224.

Mullis, Kary B. et al., eds. (1994). *PCR: The Polymerase Chain Reaction.* Birkhäuser: pp. xv-xvii (Table of Contents).

Nelson, Jeffrey S. et al. (1997). "N3'→P5' Oligodeoxyribonucleotide Phosphoramidates: A New Method of Synthesis Based on a Phosphoramidite Amino-Exchange Reaction" *J. Org. Chem.* 62:7278-7287.

Parr, Margaret B. and Parr, Earl L. (1997). "Protective Immunity Against HSV-2 in the Mouse Vagina" *J. Reprod. Immunol.* 36:77-92.

Peyrottes, Suzanne et al. (1996). "Oligodeoxynucleoside Phosphoramidates (P-NH2): Synthesis and Thermal Stability of Duplexes with DNA and RNA Targets" *Nucleic Acids Res.* 24(10):1841-1848.

Pisetsky, David S. and Reich, Charles F. (1994). "Stimulation of Murine Lymphocyte Proliferation by a Phosphorothioate Oligonucleotide with Antisense Activity for Herpes Simplex Virus" *Life Sci.* 54(2):101-107.

Pisetsky, David S. et al. (1995). "Immunological Properties of Bacterial DNA" *Ann. N.Y. Acad. Sci.* 772:152-163.

Pisetsky, David S. (1996a). "The Immunologic Properties of DNA" *J. Immunol.* 156(2):421-423.

Pisetsky, David S. (1996b). "Immune Activation by Bacterial DNA: a New Genetic Code" *Immunity* 5:303-310.

Raz, Eyal et al. (1994). "Intradermal Gene Immunization: the Possible Role of DNA Uptake in the Induction of Cellular Immunity to Viruses" *Proc. Natl. Acad. Sci. USA* 91:9519-9523.

Raz, Eyal et al. (1996). "Preferential Induction of a Th1 Immune Response and Inhibition of Specific IgE Antibody Formation by Plasmid DNA Immunization" *Proc. Natl. Acad. Sci. USA* 93:5141-5145.

Redford, Thomas W. et al. (1998). "Cyclosporin A Enhances IL-12 Production by CpG Motifs in Bacterial DNA and Synthetic Oligodeoxynucleotides" *J. Immunol.* 161:3930-3935.

Rhodes, A. J. and van Rooyen, C.E., eds. (1953). *Textbook of Virology*, 2nd ed., Williams and Wilkins: pp. 66-69.

Romagnani, Sergio (2000). "T-Cell Subsets (Th1 versus Th2)" *Ann. Allergy Asthma Immunol.* 85(1):9-18.

Roman, Mark et al. (1997). "Immunostimulatory DNA Sequences Function as T Helper-1-Promoting Adjuvants" *Nature Med.* 3(8):849-854.

Sambrook, J. et al., eds. (1989). *Molecular Cloning: A Laboratory Manual*, Second Edition, Cold Spring Harbor Laboratory Press: pp. x-xxxviii (Table of Contents).

Sato, Yukio et al. (1996). "Immunostimulatory DNA Sequences Necessary for Effective Intradermal Gene Imunnization" *Science* 273:352-354.

Schacht, Etienne et al. (1996). "Biomedical Applications of Degradable Polyphosphazenes" *Biotechnol. Bioeng.* 52:102-107.

Schulz, Ronald G. and Gryaznov, Sergei M. (1996). "Oligo-2'-Fluoro-2'-Deoxynucleotide N3'→P5 Phosphoramidates: Synthesis and Properties" *Nucleic Acids Res.* 24(15):2966-2973.

Schwartz, David A. et al. (1997). "CpG Motifs in Bacterial DNA Cause Inflammation in the Lower Respiratory Tract" *J. Clin. Invest.* 100(1):68-73.

Shimada, Shizuo et al. (1986). "*In Vivo* Augmentation of Natural Killer Cell Activity with a Deoxyribonucleic Acid Fraction of BCG" *Jpn. J. Cancer Res.* 77:808-816.

Sonehara, Kazuhiko et al. (1996). "Hexamer Palindromic Oligonucleotides with 5'-CG-3' Motif(s) Induce Production of Interferon" *J. Interferon and Cytokine Res.* 16:799-803.

Sparwasser, Tim et al. (1997). "Macrophages Sense Pathogens Via DNA Motifs: Induction of Tumor Necrosis Factor-Alpha-Mediated Shock" *Eur. J. Immunol.* 27:1671-1679.

Spiegelberg, H.L. et al. (1998). "Inhibition of IgE Formation and Allegic Inflammation by Allergen Gene Immunization and by CpG Motif Immunostimulatory Oligodeoxynucleotides" *Allergy* 53:93-97.

Spiegelberg, Hans L. et al. (1999). "Inhibition of Allergic Inflammation in the Lung by Plasmid DNA Allergen Immunization" *Pediatr. Pulmonol.* Suppl. 18:118-121.

Stacey, Katryn J. et al. (1996). "Macrophages Ingest and are Activated by Bacterial DNA" *J. Immunol.* 157(5):2116-2122.

Stanberry, Lawrence R. et al. (1986). "Genital Reinfection After Recovery from Initial Genital Infection with Herpes Simplex Vrus Type 2 in Guinea Pigs" *J. Infect. Dis.* 153(6):1055-1061.

Stanberry, Lawrence R. et al. (1988). "Herpes Simplex Virus Glycoprotein Treatment of Recurrent Genital Herpes " *J. Infect. Dis.* 157(1):156-163.

Stanberry, Lawrence R. et al. (1989). "Herpes Simplex Virus Glycoprotein Immunotherapy of Recurrent Genital Herpes: Factors Influencing Efficacy" *Antiviral Res.* 11:203-214.

Stanberry, Lawrence R. et al. (1990). "Recurrent Genital Herpes in the Guinea Pig Augmented by Ultraviolet Irradiation: Effects of Treatment with Acyclovir" *Antiviral Res.* 13:227-235.

Stanberry, L.R. (1993). "Genital and Neonatal Herpes Simplex Virus Infections: Epidemiology, Pathogenesis and Prospects for Control" *Rev. Med. Virol.* 3:37-46.

Stanberry, Lawrence R. (1995). "Herpes Simplex Virus Vaccines as Immunotherapeutic Agents" *Trends Microbiol.* 3(6):244-247.

Stein, C.A. and Krieg, Arthur (1997). "Non-Antisense Effects of Oligodeoxynucleotides" Chapter 11 in *Antisense Technology* Lichtenstein, C. and Nellen, W. eds., IRL Press: pp. 241-264.

Stirchak, Eugene P. et al. (1989). "Uncharged Stereoregular Nucleic Acid Analogs: 2. Morpholino Nucleoside Oligomers with Carbamate Internucleoside Linkages" *Nucleic Acids Res.* 17(15):6129-6141.

Stokes, A. et al. (1997). "High Level Expression of Equine Herpesvirus 1 Glucoproteins D and H and Their Role in Protection Against Virus Challenge in the C3H (H-2K$^k$) Murine Model" *Virus Res.* 50:159-173.

Straus, Stephen E. et al. (1994). "Placebo-Controlled Trial of Vaccination with Recombinant Gycoprotein D of Herpes Simplex Virus Type 2 for Immunotherapy of Genital Herpes" *The Lancet* 343:1460-1463.

Straus S. E. (1997). "Immunotherapy of Recurrent Genital Herpes with Recombinant Herpes Simplex Virus Type 2 Glycoproteins D and B: Results of a Placebo-Controlled Vaccine Trial" *J. Infect. Dis.* 176(5):1129-1134.

Tokunaga, Tohru et al. (1992). "Synthetic Oligonucleotides with Particular Base Sequences from the cDNA Encoding Proteins of *Mycobacterium bovis* BCG Induce Interferons and Activate Natural Killer Cells" *Microbiol. Immunol.* 36(1):55-66.

Uehling, David T. et al. (1991). "Immunization Against Urinary Tract Infection with a Multi-Valent Vaginal Vaccine" *J. Urol.* 146:223-226.

Uehling, David T. et al. (1994). "Vaginal Immunization of Monkeys Against Urinary Tract Infection with a Multi-Strain Vaccine" *J. Urol.* 151:214-216.

Uehling, David T. et al. (1994). "Phase I Clinical Trial of Vaginal Mucosal Immunization for Recurrent Urinary Tract Infection" *J. Urol.* 152:2308-2311.

Wang, Shaohui and Kool, Eric T. (1994). "Circular RNA Oligonucleotides. Synthesis, Nucleic Acid Binding Properties, and a Comparison with Circular DNAs" *Nucleic Acids Res.* 22(12):2326-2333.

Warner, B.D. et al. (1984). "Construction and Evaluation of an Instrument for the Automated Synthesis of Oligodeoxyribonucleotides" *DNA* 3(5):401-411.

Weeratna, Risini et al. (1998). "Reduction of Antigen Expression from DNA Vaccines by Coadministered Oligodeoxynucleotides" *Antisense and Nucleic Acid Drug Development* 8:351-356.

Weiner, George J. et al. (1997). "Immunostimulatory Oligodeoxynucleotides Containing the CpG Motif are Effective as Immune Adjuvants in Tumor Antigen Immunization" *Proc. Natl. Acad. Sci. USA* 94:10833-10837.

Weir, D.M., ed., *Handbook of Experimental Immunology in Four Volumes* "vol. 4: Applications of Immunological Methods in Biomedical Sciences" Blackwell Scientific Publications: pp. v-x (Table of Contents).

Wild, David, ed., (1994). *Immunoassay Handbook*, Stockton Press: pp. v-xvi (Table of Contents).

Wooldridge, James E. et al. (1997). "Immunostimulatory Oligodeoxynucleotides Containing CpG Motifs Enhance the Efficacy of Monoclonal Antibody Therapy of Lymphoma" *Blood* 89(8):2994-2998.

Yamamoto, Saburo et al. (1992). "Unique Palindromic Sequences in Synthetic Oligonucleotides are Required in Induce IFN [correction of INF] and Augment IFN-Mediated [correction of INF] Natural Killer Activity" *J. Immunol.* 148(12):4072-4076.

Yamamoto, Toshiko et al. (1994a). "Ability of Oligonucleotides with Certain Palindromes to Induce Interferon Production and Augment Natural Killer Cell Activity is Associated with Their Base Length" *Antisense Research and Development* 4:119-122.

Yamamoto, Toshiko et al. (1994b). "Synthetic Oligonucleotides with Certain Palindromes Stimulate Interferon Production of Human Peripheral Blood Lymphocytes in Vitro" *Jpn. J. Cancer Res.* 85:775-779.

Yi, Ae-Kyung et al. (1996). "IFN-Gamma Promotes IL-6 and IgM Secretion in Response to CpG Motifs in Bacterial DNA and Oligodeoxynucleotides" *J. Immunol.* 156(2):558-564.

Yi, Ae-Kyung et al. (1998a). "CpG DNA Rescue from Anti-IgM-Induced WEHI-231 B Lymphoma Apoptosis Via Modulation of I Kappa B Alpha and I Kappa B Beta and Sustained Activation of Nuclear Factor-Kappa B/c-Rel" *J. Immunol.* 160(3):1240-1245.

Yi, Ae-Kyung et al.(1998b). "CpG Motifs in Bacterial DNA Activate Leukocytes Through the pH-Dependent Generation of Reactive Oxygen Species" *J. Immunol.* 160(10):4755-4761.

Yi, Ae-Kyung et al. (1998c). "CpG Oligodeoxyribonucleotides Rescue Mature Spleen B Cells from Spontaneous Apoptosis and Promote Cell Cycle Entry" *J. Immunol.* 160(12):5898-5906.

Yi, Ae-Kyung et al. (1998d). "Cutting Edge: Rapid Induction of Mitogen-Activated Protein Kinases by Immune Stimulatory CpG DNA" *J. Immunol.* 161(9):4493-4497.

Zhao, Qiuyan et al. (1996). "Effect of Different Chemically Modified Oligodeoxynucleotides on Immune Stimulation" *Biochem. Pharmacol.* 51(2):173-182.

Zimmermann, Stefan et al. (1998). "CpG Oligodeoxynucleotides Trigger Protective and Curative Th1 Responses in Lethal Murine Leishmaniasis" *J. Immunol.* 160(8):3627-3630.

Zon, Gerald (1993). "Oligonucleoside Phosphorothioates" Chapter 8 *in Protocols for Oligonucleotides and Analogs, Synthesis and Properties*, Agrawal (ed.), Humana Press: pp. 165-189.

Pyles, R. et al. (2000). "Topical Immunostimulatory Sequence-Containing Oligonucleotide-Based Therapy of Genital Herpes Simplex Virus Type 2 (HSV-2) Infection" *Presented at "Microbicides 2000" Meeting*, Mar. 13-16, 2000, Washington, D.C.

Agrawal, S. and Kandinalla, E.R. (2002). "Medicinal Chemistry and Therapeutic Potential of CpG DNA," *Trends in Molecular Medicine* 8(3):114-121.

Dartmann et al. (1986). "The Nucleotide Sequence and Genome Organization of Human Papilloma Virus Type 11," *Virology* 151:124-130.

Davis, H. et al. (1998). "CpG DNA is a Potent Enhancer of Specific Immunity in Mice Immunized with Recombinant Hepatitis B Surface Antigen," *Journal of Immunology* 160(2):870-876.

Dolin. (1985). "Antiviral Chemotherapy and Chemoprophylaxis," *Science* 227:1296-1303.

Shigeta, S. (1998). "Approaches to Antiviral Chemotherapy for Acute Respiratory Infections," *Antiviral Chemistry & Chemotherapy* 9:93-107.

Stratagene. (1988). *Catalog: Gene Characterization Kits*, p. 39. (Table of Contents).

Sundaram et al. (1998). "Intracutaneous Vaccination of Rabbitis with the E6 Gene of Cottontail Rabbit Papillomavirus Provides Partial Protetion Against Virus Challenge," *Vaccine* 16(6):613-623.

Tokunaga et al. (1999). "How BCG Led to the Discovery of Immunotimulatory DNA," *Jpn. J. Infec. Dis.* 52:1-11.

Van Nest, G. et al. (1999). "An Immunostimulatory Oligonucleotide (ISS ODN) Enhances Immune Responses to HBV Vaccine in a Variety of Animal Species Including Primates," *Abstracts of the Interscience Conference of Antimicrobial Agents* p. 374, abstract No. 679.

Ashkar et al., Journal of Virology (2003) 77(16):8948-8956.

Harandi et al., Journal of Virology (2003) 77(2):953-962.

Herbst and Pyles, Journal of Antimicrobial Chemotherapy (2003) 52:887-889.

Current Drugs Ltd. (Feb. 24, 2003). "Lilly and 3M Suspend Resiquimod Trails," Located at <http://www.iddb.com/iddb3/iddb3_2/reports.print_display?i_query_id=0&template=Refe...>, last visited on Oct. 13, 2005, 1 page.

Current Drugs Ltd. (Feb. 24, 2003). "Preliminary Data from Recently Completed Clinical Trials of Resiquimod Suggest Dosing Used in Studies will not Achieve Adequate Efficacy," located at <http://www.iddb.com/iddb3/iddb3_2/reports.print_display?i_qury_id=0&template=Refe...>, last visited on Oct. 13, 2005, 1 page.

International Search Report mailed Jun. 17, 2002 for PCT Application No. PCT/US01/07839 filed Mar. 12, 2001, 4 pages.

International Search Report mailed Jun. 18, 2002 for PCT Application No. PCT/US01/07841 filed Mar. 12, 2001, 6 pages.

International Search Report mailed Jun. 17, 2002 for PCT Application No. PCT/US01/07931 filed Mar. 12, 2001, 7 pages.

International Search Report mailed Jun. 17, 2002 for PCT Application No. PCT/US01/07842 filed Mar. 12, 2001, 6 pages.

International Search Report mailed Jun. 17, 2002 for PCT Application No. PCT/US01/07840 filed Mar. 12, 2001, 6 pages.

Krieg, A.M. (Aug. 1996). "An Innate Immune Defense Mechanism Based on the Recognition of CpG Motifs in Microbial DNA," *J. Lab. Clin. Med.* 128(2):128-133.

Krieg, A.M. (2000). "The Role of CpG Motifs in Innate Immunity," *Current Opinion In Immunology* 12:35-43.

Kwant, A. et al. (2004). "Intravaginal Immunization with Viral Subunit Protein Plus CpG Oligonucleotides Induces Protective Immunity Against HSV-2," *Vaccine* 22:3098-3104.

Pisani, P. et al. (1993). "Estimates of the Worldwide Mortality from Eighteen Major Cancers in 1985. Implications for Prevention and Projections of Future Burden," *Intl. J. Cancer* 55:891-903.

Romano, G. et al. (2000). "Latest Developments in Gene Transfer Technology: Achievements, Perspectives, and Controversies over Therapeutic Applications," *Stem Cells* 18:19-39.

Silverman, E.S. et al. (2003). "Immunostimulatory DNA for Asthma: Better Than Eating Dirt," *Am. J. Respr. Cell Mol. Biol.* 28:645-647.

The University of Texas Medical Branch at Galveston. (Date Unknown). "New Drug Reduces Frequency of Genital Herpes Flare-ups," located at <http://www.utmb.edu/newsroom/01pr_archive/jul_2001/resiquimod.htm>, last visited on Nov. 17, 2005, 2 pages.

Unknown. (Date Unknown). "Resiquimod (Topical), 3M," located at <http://www.iddb.com/iddb3/iddb3_2/reports.print_display?i_query_id=5874091&template...>, last visited on Oct. 7, 2005, 1 page.

Fearon, K. et al. (2003). "A Minimal Human Immunostimulatory CpG Motif That Potently Induces IFN-Gamma and IFN-Alpha Production," *Eur. J. Immunol.* 33:2114-2212.

Kobayashi, H. et al. (1999). "Immunostimulatory DNA Pre-priming: a Novel Approach for Prolonged Th1-Biased Immunity," *Cell Immun.* 198:69-75.

Marshall, J.D. et al. (2003). "Novel Chimeric Immunomodulatory Compounds Containing Short CpG Oligodeoxyribonucleotides Have Differential Activities in Human Cells," *Nucleic Acids Research* 31(17):5122-5133.

Marshall, J.D. et al. (2005). "Superior Activity of the Type C Class of ISS in Vitro and In Vivo Across Multiple Species," *DNA and Cell Bio.* 24(2):63-72.

Hartmann, G. et al. (2000). "Mechanism and Function of a Newly Identified CpG DNA Motif in Human Primary B Cells," *J. Immunology* 164:944-952.

* cited by examiner

METHODS OF AMELIORATING SYMPTOMS OF HERPES INFECTION USING IMMUNOMODULATORY POLYNUCLEOTIDE SEQUENCES

CROSS-REFERENCE TO RELATED APPLICATIONS

This application claims the priority benefit of U.S. Provisional application 60/188,556, filed Mar. 10, 2000, which is hereby incorporated herein by reference in its entirety

TECHNICAL FIELD

This invention is in the field of immunomodulatory polynucleotides, more particularly their use in ameliorating or preventing herpes virus infection and/or symptoms of herpes virus infection.

BACKGROUND ART

Herpes viruses cause a number of significant disorders. Herpes simplex viruses (HSV) can be neurovirulent (e.g., infect and replicate in central nervous system tissue), although HSV infections of the brain are rare. HSV infections in neonates and immunosuppressed individuals can be severe. Herpes simplex virus-1 (HSV-1) is primarily responsible for orolabial herpetic lesions, although genital herpes may also be caused by HSV-1. Herpes simplex virus-2 (HSV-2) is the primary cause of genital herpes, and genital herpes caused by HSV-2 are generally more severe than genital herpes due to HSV-1. Additionally, HSV-2 represents a greater public health threat, as HSV-2 infection is associated with certain genital tract cancers and can be transmitted from mother to child during vaginal delivery.

A primary infection with the herpes virus varicella zoster virus (VZV) results in the human disease varicella, also known as chicken pox. Primary infection leads to latent infection of dorsal root ganglia cells, giving rise to a reservoir of virus which can be reactivated. Reactivation of latent VZV gives rise to a condition referred to as herpes zoster or shingles. Both primary and reactivated VZV infections give rise to cutaneous lesions, although varicella symptoms can include mucosal lesions as well.

Genital HSV-2 is among the most commonly sexually transmitted infectious diseases in women. Clinical infection occurs in 20–30% of adults (Parr et al. (1997) *J. Reprod. Immunol.* 36:77–92; Burke et. al. (1994) *J. Infect. Dis.* 170:1110–1119), while up to 85% of females can develop HSV-2 antibodies in their lifetime (Kinghorn (1996) *Scand. J. Infect. Dis. Suppl.* 100:20–25). The frequency of recurrences can be as often as monthly, at times lasting several days. Stanberry et al. (1986) *J. Infect. Dis.* 153:1055–1061. Complications may be significant, frequently resulting in sociopathologic morbidity, adenopathy, encephalitis neurologic syndromes. Neonatal infection may be high as 1:2000 births, usually caused by retrograde spread of HSV-2 or from fetal passage through an infected genital tract. Mortality (up to 85% in untreated infected newborns) results from disseminated intravascular coagulation, destructive encephalitis and other neurological maladies. Stanberry (1993) *Rev. Med. Virol.* 3:37–46.

The incidence of genital HSV-2 continues to escalate. An estimated 700,000 new cases occur each year in the U.S. alone. Reactivation is common, resulting in an estimated 25 million cases of recurrent genital herpes each year. Transmission commonly occurs through unprotected sexual contact, particularly during periods of asymptomatic viral shedding, and results in heightened morbidity and mortality when perinatal fetal transmission occurs. Current treatment of genital HSV-2 includes antiviral drugs that are merely palliative, controlling symptoms and exacerbations without providing a cure. Additionally, these chemotherapeutics are costly and may be associated with adverse reactions and potential drug interactions. Vaccines are a more desirable alternative to drug treatment or prophylaxis, and have been developed against HSV-2 to limit transmission or recurrence. Specific vaccines that have shown efficacy in animal models and clinical studies used attenuated virus, recombinant HSV-2 surface proteins or their corresponding cDNA. Their utility, however, is counterbalanced by the need of parenteral administration, often with poorly tolerated and unapproved adjuvants, and with less than desired clinical efficacy in humans and patient acceptability.

Clinical control of HSV-2 currently is limited to the use of topical, oral or intravenous antiviral drugs. These agents may be effective in controlling symptoms, and may diminish transmission and recurrence rates, but are not curative. These drugs also do not prevent transmission, particularly during asymptomatic viral shedding. Clear prevention of transmission or recurrence from latency would be a preferred method of clinical control. Immunologic prophylaxis against HSV-2 through vaccination has, therefore, emerged as a therapeutic alternative to chemotherapy. More specifically, highly targeted immunogenic components responsible for virus-host propagation, such as glycoprotein D, have provided the most appropriate strategy for immunization. Stokes et al. (1997) *Virus Res.* 50:159–174.

A host of studies using attenuated or inactive viruses or their components have demonstrated some utility as vaccines. Stanberry (1995) *Trends Microbiol.* 3:244–247. More recently, recombinant HSV-2 surface protein vaccines, particularly HSV-2 glycoprotein D (gD2), have shown greater efficacy in stimulating immune responses while limiting duration and severity of recurrences. Stanberry et al. (1988) *J. Infect. Dis.* 157:156–163; Straus (1994) *Lancet* 343: 1460–1463; Straus (1997) *J. Infect. Dis.* 176:1129–1134; Langenberg (1995) *Ann. Intern. Med.* 122:889–898. The gD2 is an integral membrane protein, present in the viral envelope and is required for viral attachment and subsequent propagation in the host cell. The mature protein is composed of 368 residues, the C-terminal portion containing the transmembrane region. Multiple glycosylation sites (three N-linked and two to three O-linked) exist. While peptide fragments or bacterially-expressed expressed gD proteins possess antigenic properties, glycosylation appears necessary in eliciting maximal immunogenic responses, suggesting that eukaryotic cell expression vectors are more appropriate for generating this protein antigen. Stokes et al. (1997); Damhoff et al. (1994) *J. Chromatogr.* 676:43–49.

Others have demonstrated that nucleic acid vaccines, such as plasmid DNA encoding gD2, can also effectively immunize against HSV-2 by stimulation of both cellular and humoral immune responses. Bourne et al. (1996) *J. Infect. Dis.* 173:800–807; Bourne et al. (1996) *Vaccine* 14:1230–1234. However, all these vaccines were designed for parenteral administration, often containing unapproved or poorly tolerated adjuvants.

Meanwhile, nontraditional routes of antigen delivery, such as mucosal vaccination, have emerged as effective immunization alternatives. A body of evidence suggests that mucosal vaccination may provide more effective immunization against pathogens such as HSV-2, in essence, by inhibiting cellular attachment or neutralizing toxins at the point of exposure, e.g., within the genital mucosa, prior to pathogen and host interaction. Clements (1997) *Nature Biotech.* 15:622–623. These immune responses were amplified significantly with co-administration of adjuvants, such as cholera toxin β-subunit.

The concept of providing immune protection specifically through vaginal vaccination also has been proposed to be an effective alternative to parenteral vaccination. Parr et al. (1997); Clements (1997) *Nature Biotech.* 71:1497–1504; Uehling et al. (1991) *J. Urol.* 146:223; Uehling et al. (1994) *J. Urol.* 152:2308–2311; Uehling et al. (1994) *J. Urol.* 151:213. In animal models, this route of vaccination using inactivated urinary tract pathogens resulted in an increased IgA response in vaginal and urinary secretions with a decrease in clinically apparent re-infection. Uehling et al. (1991); Uehling et al. (1994) *J. Urol.* 151:213. Similarly in mice, attenuated strains of HSV-2 applied intravaginally induced humoral (particularly, immunization-stimulated IgG) and cellular immunity in both sera and vaginal secretions. Parr et al. (1997); McDermott et al. (1970) *J. Gen. Virol.* 71:1497–1504. Vaginally-administered mucosal adjuvants, in particular cholera toxin β-subunit, significantly raise IgA and IgG levels in the genital mucosa. (Johannsson et al. (1998) *Inf. Immun.* 66:514–520. These studies support the concept that mucosal associated lymphoid tissue participates in the generation of local immune-mediated protection. Furthermore, unlike parenteral vaccines, mucosal vaccination, such as a vaginal delivery, precludes the necessity of a pyrogen-free vaccine, causes fewer adverse reactions, and is amenable to routine booster immunizations.

Administration of certain DNA sequences, generally known as immunostimulatory sequences or "ISS," induces an immune response with a Th1-type bias as indicated by secretion of Th1-associated cytokines. The Th1 subset of helper cells is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets See, for example, Romagnani (2000) *Ann. Allergy Asthma Immunol.* 85:9–18.

Administration of an immunostimulatory polynucleotide with an antigen results in a Th1-type immune response to the administered antigen. Roman et al. (1997) *Nature Med.* 3:849–854. For example, mice injected intradermally with *Escherichia coli* (*E. coli*) β-galactosidase (β-Gal) in saline or in the adjuvant alum responded by producing specific IgG1 and IgE antibodies, and $CD4^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and $CD4^+$ cells that secreted IFN-γ, but not IL-4 and IL-5, demonstrating that the T cells were predominantly of the Th1 subset. Moreover, specific IgE production by the plasmid DNA-injected mice was reduced 66–75%. Raz et al. (1996) *Proc. Natl. Acad. Sci. USA* 93:5141–5145 In general, the response to naked DNA immunization is characterized by production of IL-2, TNFα and IFN-γ by antigen-stimulated $CD4^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Other references describing ISS include: Krieg et al. (1989) *J. Immunol.* 143:2448–2451; Tokunaga et al. (1992) *Microbiol. Immunol.* 36:55–66; Kataoka et al. (1992) *Jpn. J. Cancer Res.* 83:244–247; Yamamoto et al. (1992) *J. Immunol.* 148:4072–4076; Mojcik et al. (1993) *Clin. Immuno. and Immunopathol.* 67:130–136; Branda et al. (1993) *Biochem. Pharmacol.* 45:2037–2043; Pisetsky et al. (1994) *Life Sci.* 54(2):101–107; Yamamoto et al. (1994a) *Antisense Research and Development.* 4:119–122; Yamamoto et al. (1994b) *Jpn. J. Cancer Res.* 85:775–779; Raz et al. (1994) *Proc. Natl. Acad. Sci. USA* 91:9519–9523; Kimura et al. (1994) *J. Biochem.* (Tokyo) 116:991–994; Krieg et al. (1995) *Nature* 374:546–549; Pisetsky et al. (1995) *Ann. N.Y. Acad. Sci.* 772:152–163; Pisetsky (1996a) *J. Immunol.* 156:421–423; Pisetsky (1996b) *Immunity* 5:303–310; Zhao et al. (1996) *Biochem. Pharmacol.* 51:173–182; Yi et al. (1996) *J. Immunol.* 156:558–564; Krieg (1996) *Trends Microbiol.* 4(2):73–76; Krieg et al. (1996) *Antisense Nucleic Acid Drug Dev.* 6:133–139; Klinman et al (1996) *Proc. Natl. Acad. Sci. USA.* 93:2879–2883; Raz et al. (1996); Sato et al. (1996) *Science* 273:352–354; Stacey et al. (1996) *J. Immunol.* 157:2116–2122; Ballas et al. (1996) *J. Immunol.* 157:1840–1845; Branda et al. (1996) *J. Lab. Clin. Med.* 128:329–338; Sonehara et al. (1996) *J. Interferon and Cytokine Res.* 16:799–803; Klinman et al. (1997) *J. Immunol.* 158:3635–3639; Sparwasser et al. (1997) *Eur. J. Immunol.* 27:1671–1679; Roman et al. (1997); Carson et al. (1997) *J. Exp. Med.* 186:1621–1622; Chace et al. (1997) *Clin. Immunol. and Immunopathol.* 84:185–193; Chu et al. (1997) *J. Exp. Med.* 186:1623–1631; Lipford et al. (1997a) *Eur. J. Immunol.* 27:2340–2344; Lipford et al. (1997b) *Eur. J. Immunol.* 27:3420–3426; Weiner et al. (1997) *Proc. Natl. Acad. Sci. USA* 94:10833–10837; Macfarlane et al. (1997) *Immunology* 91:586–593; Schwartz et al. (1997) *J. Clin. Invest.* 100:68–73; Stein et al. (1997) *Antisense Technology,* Ch. 11 pp. 241–264, C. Lichtenstein and W. Nellen, Eds., IRL Press; Wooldridge et al. (1997) *Blood* 89:2994–2998; Leclerc et al. (1997) *Cell. Immunol.* 179:97–106; Kline et al. (1997) *J. Invest. Med.* 45(3):282A; Yi et al. (1998a) *J. Immunol.* 160:1240–1245; Yi et al. (1998b) *J. Immunol.* 160:4755–4761; Yi et al. (1998c) *J. Immunol.* 160:5898–5906; Yi et al. (1998d) *J. Immunol.* 161:4493–4497; Krieg (1998) *Applied Antisense Oligonucleotide Technology* Ch. 24, pp. 431–448, C. A. Stein and A. M. Krieg, Eds., Wiley-Liss, Inc.; Krieg et al. (1998a) *Trends Microbiol.* 6:23–27; Krieg et al. (1998b) *J. Immunol.* 161:2428–2434; Krieg et al. (1998c) *Proc. Natl. Acad. Sci. USA* 95:12631–12636; Spiegelberg et al. (1998) *Allergy* 53(45S):93–97; Homer et al. (1998) *Cell Immunol.* 190:77–82; Jakob et al. (1998) *J. Immunol.* 161:3042–3049; Redford et al. (1998) *J. Immunol.* 161:3930–3935; Weeratna et al. (1998) *Antisense & Nucleic Acid Drug Development* 8:351–356; McCluskie et al. (1998) *J. Immunol.* 161(9):4463–4466; Gramzinski et al. (1998) *Mol. Med.* 4:109–118; Liu et al. (1998) *Blood* 92:3730–3736; Moldoveanu et al. (1998) *Vaccine* 16: 1216–1224; Brazolot Milan et al (1998) *Proc. Natl. Acad. Sci. USA* 95:15553–15558; Broide et al. (1998) *J. Immunol.* 161:7054–7062; Broide et al. (1999) *Int. Arch. Allergy Immunol.* 118:453–456; Kovarik et al. (1999) *J. Immunol.* 162:1611–1617; Spiegelberg et al. (1999) *Pediatr. Pulmonol. Suppl.* 18:118–121; Martin-Orozco et al. (1999) *Int. Immunol.* 11:1111–1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291–2298, WO 98/52962, WO 99/33488, WO 99/33868, WO 99/51259 and WO 99/62923. See also Zimmermann et al. (1998) *J. Immunol.* 160:3627–3630; Krieg (1999) *Trends Microbiol.* 7:64–65; U.S. Pat. Nos. 5,663,153, 5,723,335, 5,849,719 and 6,174,872. See also WO 99/56755, WO 00/06588, WO 00/16804; WO 00/21556; WO 00/67023 and WO 01/12223.

There exists a need in the art for effective treatments of herpes virus infections.

All publications and patent applications cited herein are hereby incorporated by reference in their entirety.

DISCLOSURE OF THE INVENTION

The invention provides methods of suppressing, ameliorating and/or preventing herpes virus infection in an individual using immunostimulatory polynucleotide sequences. Accordingly, in one aspect, the invention provides methods of preventing, palliating, ameliorating, reducing and/or eliminating one or more symptoms of herpes virus infection, preferably herpes simplex virus infection, without administering an alphaherpesvirinae antigen. A polynucleotide comprising an immunostimulatory sequence (an "ISS") is administered to an individual who is at risk of being exposed to alphaherpesvirinae, has been exposed to alphaherpesvirinae or is infected with alphaherpesvirinae. The ISS-containing polynucleotide is administered without any alphaherpesvirinae antigens (i.e., alphaherpesvirinae antigen is not co-administered). Administration of the ISS results in reduced incidence, recurrence, and/or severity of one or more symptoms of alphaherpesvirinae infection.

In one embodiment, the invention provides methods for preventing a symptom of alphaherpesvirinae infection in an individual at risk of being exposed to alphaherpesvirinae which entail administering an effective amount of a composition comprising a polynucleotide comprising an immunostimulatory sequence (ISS) (i.e., an amount of the composition sufficient to prevent a symptom of alphaherpesvirinae infection) to the individual, wherein the ISS comprises the sequence 5'-C, G-3' and wherein an alphaherpesvirinae antigen is not administered in conjunction with administration of the composition (i.e., antigen is not administered with the ISS-containing polynucleotide), thereby preventing a symptom of alphaherpesvirinae infection.

Another embodiment of the invention provides methods for preventing a symptom of alphaherpesvirinae infection in an individual who has been exposed to alphaherpesvirinae which entail administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby preventing a symptom of alphaherpesvirinae infection.

Another embodiment of the invention provides methods of reducing severity of a symptom of alphaherpesvirinae infection in an individual infected with alphaherpesvirinae by administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby reducing severity of a symptom of alphaherpesvirinae infection. In a further embodiment, the invention provides methods of reducing the level of viral shedding in an infected individual with alphaherpesvirinae, such as HSV-1 or HSV-2.

Another embodiment of the invention provides methods of suppressing an alphaherpesvirinae infection in an individual infected with or at risk of being infected with alphaherpesvirinae which entail administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby suppressing an alphaherpesvirinae infection.

Another embodiment of the invention provides methods of delaying development of an alphaherpesvirinae infection and/or a symptom of alphaherpesvirinae infection in an individual infected or at risk of being infected with alphaherpesvirinae which entail administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby delaying development of an alphaherpesvirinae infection and/or a symptom of alphaherpesvirinae infection.

Another embodiment of the invention provides methods of reducing duration of an alphaherpesvirinae infection in an individual infected or at risk of being infected with alphaherpesvirinae which entail administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby delaying development of an alphaherpesvirinae infection.

In another embodiment, the invention provides methods of reducing recurrence of a symptom of alphaherpesvirinae infection in an individual infected with alphaherpesvirinae which entail administering an effective amount of a composition comprising a polynucleotide comprising an ISS to the individual, wherein the ISS comprises the sequence 5'-C, G-3' and wherein an alphaherpesvirinae antigen is not administered in conjunction with administration of the composition, thereby reducing recurrence of a symptom of alphaherpesvirinae infection.

In another aspect, the invention provides kits for use in ameliorating and/or preventing a symptom of alphaherpesvirinae infection in an individual infected with, exposed to or at risk of being exposed to alphaherpesvirinae. The kits comprise a composition comprising a polynucleotide comprising an ISS, wherein the ISS comprises the sequence 5'-C, G-3' and wherein the kit does not comprise an alphaherpesvirinae antigen, and the kits comprise instructions for administration of the composition to an individual infected with, exposed to or at risk of being exposed to alphaherpesvirinae.

In some embodiments of the methods and kits of the invention, the ISS comprises the sequence 5'-purine, purine, C, G, pyrimidine, pyrimidine, C, G-3' or 5'-purine, purine, C, G, pyrimidine, pyrimidine, C, C-3'. In further embodiments of the methods and kits, the ISS comprises a sequence selected from the group consisting of AACGTTCC, AACGTTCG, GACGTTCC, and GACGTTCG.

In some embodiments of the methods and kits of the invention, the ISS comprises the sequence 5'-T, C, G-3'. In some embodiments of the methods and kits of the invention, the ISS comprises the sequence TGACTGTGAACGTTC-GAGATGA (SEQ ID NO:1).

In some embodiments of the methods and kits of the invention, the individual is a mammal. In further embodiments, the mammal is human.

In some embodiments of the methods and kits of the invention, the alphaherpesvirinae is a herpes simplex virus. In futher embodiments of the methods and kits of the invention, the herpes simplex virus is a herpes simplex virus 1 (HSV-1) virus or a herpes simplex virus 2 (HSV-2) virus.

In some embodiments of the methods and kits of the invention, the alphaherpesvirinae is varicella zoster virus (VZV).

MODES FOR CARRYING OUT THE INVENTION

Figure 1:
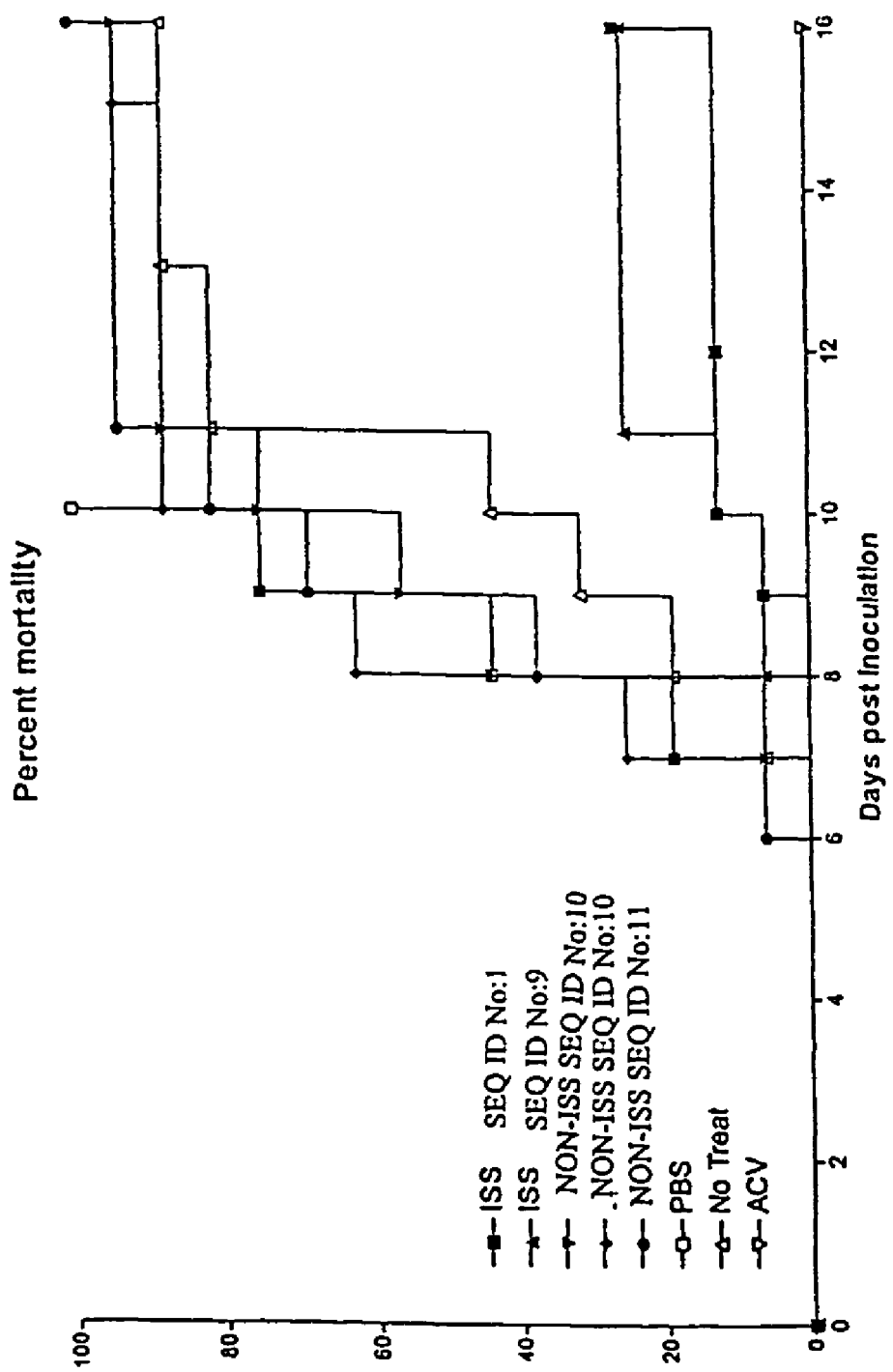
FIG. 1 summarizes results of ISS treatment of mice infected with HSV-2. The graph depicts animal survival following a lethal challenge dose of HSV-2 and subsequent treatment regimens. Animals that received an ISS treatment demonstrated improved survival as compared to animals that received non-ISS oligonucleotide treatments, PBS or no treatment.

We have discovered methods of preventing and/or treating herpes virus infections. The invention provides methods of using immunomodulatory polynucleotides that induce anti-viral cell-mediated immune responses and promote anti-herpes virus effects. The methods described herein are applicable to alphaherpesvirinae, (e.g., herpes simplex viruses as well as varicella zoster virus), and are particularly applicable to preventing and/or treating herpes simplex virus infection. A polynucleotide comprising an immunostimulatory sequence (an "ISS") is administered to an individual who is at risk of being exposed to alphaherpesvirinae, has been exposed to alphaherpesvirinae or is infected with alphaherpesvirinae. Administration of the ISS without co-administration of a herpes virus antigen results in reduced incidence, recurrence and/or severity of one or more symptoms of alphaherpesvirinae infection in an animal model of herpes virus infection.

The invention also relates to kits for ameliorating and/or preventing a symptom of herpes virus infection in exposed individuals. The kits, which do not contain an alphaherpesvirinae antigen, comprise a polynucleotide comprising an ISS and instructions describing the administration of an ISS-containing polynucleotide to an individual for the intended treatment.

As the Examples illustrate, administration of ISS to an art-accepted model of herpes virus infection in mice, namely mice infected with HSV-2, we have shown that treatment with ISS resulted in decreased incidence (i.e., individuals showing symptoms of HSV-2 infection), improved survival and delays in both appearance of symptoms and time to death in symptomatic individuals. Additionally, in an art-accepted model of acute and recurrent herpes simplex virus disease, namely guinea pigs infected with HSV-2, we have shown that treatment with ISS resulted in a significant reduction of lesion recurrences and a significant reduction in the level of viral shedding. An advantage to a reduction in viral shedding. Since the level of virus shedding is correlated with viral transmission, ISS treatment may be effective in a reduction in viral transmission. Significantly, in contrast to previous reports of immune modulation by ISS, we report clinical efficacy of ISS in this viral context.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993).

Definitions

The term "herpes virus" refers to a virus which is a member of the family herpesviridae. Herpes viruses comprise a linear DNA genome contained in a capsid. The capsid comprises 162 capsomeres and is approximately 100–110 nm in diameter. The capsid is surrounded by an amorphous tegument and enclosed by a envelope covered with viral glycoprotein spikes. "Human" herpes viruses (i.e., herpes viruses which infect human cells) include herpes simplex virus 1 (HSV-1, also known as human herpesvirus 1), herpes simplex virus 2 (HSV-2, also known as human herpesvirus 2), varicella-zoster virus (VZV, also known as human herpesvirus 3), Epstein-Barr virus (EBV, also known as human herpesvirus 4), cytomegalovirus (CMV, also known as human herpesvirus 5), as well as human herpesviruses 6, 7, and 8. HSV-1, HSV-2 and VZV are human members of the subfamily alphaherpesvirinae. "Varicella zoster virus" or "VZV" refers to VZV which infects human cells. Alphaherpesvirinae are characterized by a short reproductive cycle, efficient destruction of infected cells, and the ability to establish latent infections. Active alphaherpesvirinae infections result in cutaneous, mucosal and/or sensory neuron lesions.

"Herpes simplex viruses" include HSV-1 and HSV-2.

"Exposure" to a virus denotes encounter with virus which allows infection, such as, for example, upon contact with an infected individual.

An individual is "seronegative" for a virus if antibodies specific to the virus cannot be detected in blood or serum samples from the individual using methods standard in the art, such as ELISA. Conversely, an individual is "seropositive" for a virus if antibodies specific for the virus can be detected in blood or serum samples from the individual using methods standard in the art, such as ELISA. An individual is said to "seroconvert" for a virus when antibodies to the virus can be detected in blood or serum from an individual who was previously seronegative.

An individual who is "at risk of being exposed" to a herpes virus is an individual who may encounter the virus such that the virus infects the individual (i.e., virus enters cells and replicates). In the context of HSV-1, given the high prevalence of HSV-1 infection, an individual at risk of being exposed to HSV-1 is any individual who is seronegative for HSV-1. In the context of HSV-2, an individual at risk of being exposed to the virus is an individual who is seronegative for HSV-2 and who is engaging in one or more high risk behaviors (i.e., oral sex or sexual relations without the use of barrier prophylactics). An individual at risk of being exposed to VZV is an individual who comes in close proximity to another individual who has active primary or recurrent VZV lesions.

"Suppressing" herpes virus infection indicates any aspect of viral infection, such as viral replication, time course of infection, amount (titer) of virus, lesions, and/or one or more symptoms is curtailed, inhibited, or reduced (in terms of severity and/or duration) in an individual or a population of individuals treated with an ISS-containing polynucleotide in accordance with the invention as compared to an aspect of viral infection in an individual or a population of individuals not treated in accordance with the invention. Reduction in viral titer includes, but is not limited to, elimination of the virus from an infected site or individual. Viral infection can be assessed by any means known in the art, including, but not limited to, measurement of virus particles, viral nucleic acid or viral antigens and detection of one or more symptoms of viral infection and detection and/or measurement of anti-virus antibodies. Anti-virus antibodies are widely used to detect and monitor viral infection and generally are commercially available.

"Palliating" a disease or one or more symptoms of a disease or infection means lessening the extent and/or time course of undesirable clinical manifestations of a disease state or infection in an individual or population of individuals treated with an ISS in accordance with the invention.

As used herein, "delaying" development of a viral infection or a symptom of viral infection means to defer, hinder, slow, retard, stabilize, and/or postpone development of the disease or symptom when compared to not using the method(s) of the invention. This delay can be of varying lengths of time, depending on the history of the disease and/or individual being treated. As is evident to one skilled in the art, a sufficient or significant delay can, in effect, encompass prevention, in that the individual does not develop the disease.

"Reducing severity of a symptom" or "ameliorating a symptom" of viral infection means a lessening or improvement of one or more symptoms of viral infection as compared to not administering an ISS-containing polynucleotide. "Reducing severity" also includes shortening or reduction in duration of a symptom. For alphaherpesvirinae, these symptoms are well known in the art and include, but are not limited to, cutaneous or mucosal lesions (e.g., cutaneous, oral or genital herpetic sores) and viral shedding (e.g., virus excretion).

"Reducing duration of viral infection" means the length of time of viral infection (usually indicated by symptoms) is reduced, or shortened, as compared to not administering an ISS-containing polynucleotide.

"Preventing a symptom of infection" by a herpes virus means that the symptom does not appear after exposure to the virus.

"Reducing recurrence" refers to a reduction in frequency, severity and/or quantity of one or more recurrent viral symptoms in an infected individual or a population of infected individuals When applied to a population of individuals, "reducing recurrence" means a reduction in the mean or median frequency, severity, quantity and/or duration of recurrent viral symptoms.

The term "infected individual", as used herein, refers to an individual who has been infected by a herpes virus. For alphaherpesvirinae, symptoms of infection include seropositivity (for any of the alphaherpesvirinae), orolabial herpetic lesions (for HSV-1), genital herpetic lesions (for HSV-2 and occasionally for HSV-1), the disease varicella, also known as the chicken pox (for VZV), as well as other symptoms known in the art.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Viral titer" is a term well known in the art and indicates the amount of virus in a given biological sample. Amount of virus are indicated by various measurements, including, but not limited to, amount of viral nucleic acid; presence of viral particles; replicating units (RU); plaque forming units (PFU). Generally, for fluid samples such as blood and urine, amount of virus is determined per unit fluid, such as milliliters. For solid samples such as tissue samples, amount of virus is determined per weight unit, such as grams. Methods for determining amount of virus are known in the art and described herein.

An "individual" is a vertebrate, preferably a mammal, more preferably a human. Mammals include, but are not limited to, humans, farm animals, sport animals, rodents, primates and certain pets. Vertebrates also include, but are not limited to, birds (i.e., avian individuals) and reptiles (i.e., reptilian individuals).

The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$ T lymphocytes, B lymphocytes, and the like. Preferably, the ISS sequences preferentially activate a Th1-type response. A polynucleotide for use in methods of the invention contains at least one ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The polynucleotide can be linearly or circularly configured, or the polynucleotide can contain both linear and circular segments.

"Adjuvant" refers to a substance which, when added to an immunogenic agent such as antigen, nonspecifically enhances or potentiates an immune response to the agent in the recipient host upon exposure to the mixture.

An "effective amount" or a "sufficient amount" of a substance is an amount sufficient to effect beneficial or desired results, including clinical results. An effective amount can be administered in one or more administrations. A "therapeutically effective amount" is an amount to effect beneficial clinical results, including, but not limited to, alleviation of one or more symptoms associated with viral infection as well as prevention of disease (e.g., prevention of one or more symptoms of infection).

A microcarrier is considered "biodegradable" if it is degradable or erodable under normal mammalian physiological conditions. Generally, a microcarrier is considered biodegradable if it is degraded (i.e., loses at least 5% of its mass and/or average polymer length) after a 72 hour incubation at 37° C. in normal human serum. Conversely, a microcarrier is considered "nonbiodegradable" if it is not degraded or eroded under normal mammalian physiological conditions. Generally, a microcarrier is considered nonbiodegradable if it not degraded (i.e., loses less than 5% of its mass and/or average polymer length) after at 72 hour incubation at 37° C. in normal human serum.

The term "immunostimulatory sequence-microcarrier complex" or "ISS-MC complex" refers to a complex of an ISS-containing polynucleotide and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the ISS.

As used herein, the term "comprising" and its cognates are used in their inclusive sense; that is, equivalent to the term "including" and its corresponding cognates.

As used herein, the singular form "a", "an", and "the" includes plural references unless indicated otherwise. For example, "a" symptom of viral infection includes one or more additional symptoms.

Methods of the Invention

The invention provides methods for preventing one or more symptoms of herpes virus infection, treating, reducing severity of and/or delaying development of one or more symptoms of herpes virus infection and reducing recurrence of one or more symptoms of herpes virus infection by administering an ISS-containing polynucleotide (used interchangeably herein with "ISS") to an individual without administering a herpes virus antigen. The herpes virus may be any of the alphaherpesvirinae, preferably one of the herpes simplex viruses. An ISS-containing composition which does not include a herpes virus antigen is administered to an individual at risk of exposure to, exposed to, infected with and/or exhibiting one or more symptoms of infection by alphaherpesvirinae. Individuals receiving ISS are preferably mammal, more preferably human. In accordance with the invention, herpes virus antigen is not administered to the individual in conjunction with administration of an ISS (i.e., is not administered in a separate administration at or about the time of administration of the ISS). In some embodiments, the level (e.g., magnitude or amount) of viral shedding is reduced after administration of ISS.

In some embodiments, the individual is at risk of being exposed to virus. Determination of an at risk individual is based on one or more factors that are associated with disease development and are generally known by, or can be assessed by, a skilled clinician. At risk individuals may be especially suitable candidates to receive ISS, as these individuals are generally considered to be particularly susceptible to developing symptoms of infection, which could also further lead to other complications. For example, in the context of HSV-1 infection, any non-infected individual is considered at risk, due to the wide spread prevalence of HSV-1 infection. In the context of HSV-2 infection, an individual at risk is an individual who practices unsafe sexual practices (e.g., engages in oral-genital or genital—genital contact without the use of barrier-type prophylactics). Other examples of at risk individuals are those who are immunocompromised. An individual at risk of being exposed to VZV is an individual who comes in close proximity to another individual who has active primary or recurrent VZV lesions.

In other embodiments, the individual is, or has been, exposed to and/or infected by virus. Exposure to virus is generally indicated by sufficient contact with an infected individual or infected location. Exposure can also be indicated by development of one or more symptoms associated with viral infection. Infection by virus may be indicated by any of the above, as well as detection of virus or anti-virus antibodies (i.e., the individual becomes seropositive) in a biological sample from the individual.

ISS

The methods of this invention entail administering a polynucleotide comprising an ISS (or a composition comprising such a polynucleotide). In accordance with the present invention, the immunomodulatory polynucleotide contains at least one ISS, and can contain multiple ISSs. The ISSs can be adjacent within the polynucleotide, or they can be separated by additional nucleotide bases within the polynucleotide. Alternately, multiple ISSs may be delivered as individual polynucleotides.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995); Yamamoto et al. (1992); Ballas et al. (1996); Klinman et al. (1997); Sato et al. (1996); Pisetsky (1996a); Shimada et al. (1986) *Jpn. J. Cancer Res.* 77:808–816; Cowdery et al. (1996) *J. Immunol.* 156:4570–4575; Roman et al. (1997); and Lipford et al. (1997a).

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is unmethylated. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may comprise (i.e., contain one or more of) the sequence 5'-T, C, G-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrimidine, pyrimidine-3'.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 8; 10; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

In some embodiments, the ISS comprises any of the following sequences: GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG; AACGTTCG; AACGCTCG; GGCGTTCG; GGCGCTCG; GGCGTCCG; GGCGCCCG. In some embodiments, the immunomodulatory polynucleotide comprises the sequence 5'-TGACTGTGAACGTTCGAGATGA-3' (SEQ ID NO:1).

In some embodiments, the ISS comprises any of the following sequences: GACGCU; GACGUC; GACGUU; GACGUT; GACGTU; AGCGUU; AGCGCU; AGCGUC; AGCGUT; AGCGTU; AACGUC; AACGUU; AACGCU; AACGUT; AACGTU; GGCGUU; GGCGCU; GGCGUC; GGCGUT; GGCGTU.

In some embodiments, the ISS comprises any of the following sequences: GABGCTCC; GABGTCCC; GABGTTCC; GABGCCCC; AGBGTTCC; AGBGCTCC; AGBGTCCC; AGBGCCCC; AABGTCCC; AABGCCCC; AABGTTCC; AABGCTCC; GGBGTTCC; GGBGCTCC; GGBGTCCC; GGBGCCCC; GABGCTCG; GABGTCCG; GABGCCCG; GABGTTCG; AGBGCTCG; AGBGTTCG; AGBGTCCG; AGBGCCCG; AABGTCCG; AABGCCCG; AABGTTCG; AABGCTCG; GGBGTTCG; GGBGCTCG; GGBGTCCG; GGBGCCCG; GABGCTBG; GABGTCBG; GABGCCBG; GABGTTBG; AGBGCTBG; AGBGTTBG; AGBGTCBG; AGBGCCBG; AABGTCBG; AABGCCBG; AABGTTBG; AABGCTBG; GGBGTTBG; GGBGCTBG; GGBGTCBG; GGBGCCBG, where B is 5-bromocytosine.

In some embodiments, the ISS comprises any of the following sequences: GABGCUCC; GABGUCCC; GABGUTCC; GABGTUCC; GABGUUCC; AGBGUUCC; AGBGTUCC; AGBGUTCC; AGBGCUCC; AGBGUCCC; AABGUCCC; AABGUUCC; AABGUTCC; AABGTUCC; AABGCUCC; GGBGUUCC; GGBGUTCC; GGBGTUCC; GGBGCUCC; GGBGUCCC; GABGCUCG; GABGUCCG; GABGUUCG; GABGUTCG; GABGTUCG; AGBGCUCG; AGBGUUCG; AGBGUTCG; AGBGTUCG; AGBGUCCG; AABGUCCG; AABGUUCG; AABGTUCG; AABGCUCG; GGBGUUCG; GGBGUTCG; GGBGCUCG; GGBGUCCG; GABGCUBG; GABGUCBG; GABGUUBG; GABGUTBG; GABGTUBG; AGBGCUBG; AGBGUUBG; AGBGUCBG; AGBGUTBG; AGBGTUBG; AGBGCUBG; AABGUCBG; AABGUUBG; AABGUTBG; AABGTUBG; AABGCUBG; GGBGUUBG; GGBGUTBG; GGBGTUBG; GGBGCUBG; GGBGUCBG, where B is 5-bromocytosine.

In other embodiments, the ISS comprises any of the sequences:

5'-TGACCGTGAACGTTCGAGATGA-3' (SEQ ID NO:2);

5'-TCATCTCGAACGTTCCACAGTCA-3' (SEQ ID NO:3);

5'-TGACTGTGAACGTTCCAGATGA-3' (SEQ ID NO:4);

5'-TCCATAACGTTCGCCTAACGTTCGTC-3' (SEQ ID NO:5);

5'-TGACTGTGAABGTTCCAGATGA-3' (SEQ ID NO:6), where B is 5-bromocytosine;

5'-TGACTGTGAABGTTCGAGATGA-3' (SEQ ID NO:7), where B is 5-bromocytosine and

5'-TGACTGTGAABGTTBGAGATGA-3' (SEQ ID NO:8), where B is 5-bromocytosine.

In some embodiments, the immunomodulatory polynucleotide comprises the sequence 5'-TCGTCGAACGTTCGTTAACGTTCG-3' (SEQ ID NO:9).

An ISS and/or ISS-containing polynucleotide may contain modifications. Modifications of ISS include any known in the art, but are not limited to, modifications of the 3'-OH or 5'-OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, polynucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger polynucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Polynucleotide degradation can be accomplished through the exposure of an polynucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025–2029; and Wang et al. (1994) *Nucleic Acids Res.* 22:2326–2333.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing polynucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in *Protocols for Oligonucleotides and Analogs, Synthesis and Properties* (Agrawal, ed.) Humana Press, Totowa, N.J.; Warner et al. (1984) *DNA* 3:401 and U.S. Pat. No. 4,458,066.

The ISS can also contain phosphate-modified polynucleotides. Synthesis of polynucleotides containing modified phosphate linkages or non-phosphate linkages is also know in the art. For a review, see Matteucci (1997) "Oligonucleotide Analogs: an Overview" in *Oligonucleotides as Therapeutic Agents*, (D. J. Chadwick and G. Cardew, ed.) John Wiley and Sons, New York, N.Y. The phosphorous derivative (or modified phosphate group) which can be attached to the sugar or sugar analog moiety in the polynucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and polynucleotides, per se, is also known and need not be described here in detail. Peyrottes et al. (1996) *Nucleic Acids Res.* 24:1841–1848; Chaturvedi et al. (1996) *Nucleic Acids Res.* 24:2318–2323; and Schultz et al. (1996) *Nucleic Acids Res.* 24:2966–2973. For example, synthesis of phosphorothioate polynucleotides is similar to that described above for naturally occurring polynucleotides except that the oxidation step is replaced by a sulfurization step (Zon (1993) "Oligonucleoside Phosphorothioates" in *Protocols for Oligonucleotides and Analogs, Synthesis and Properties* (Agrawal, ed.) Humana Press, pp. 165–190). Similarly the synthesis of other phosphate analogs, such as phosphotriester (Miller et al. (1971) *JACS* 93:6657–6665), non-bridging phosphoramidates (Jager et al. (1988) *Biochem.* 27:7247–7246), N3' to P5' phosphoramidates (Nelson et al. (1997) *JOC* 62:7278–7287) and phosphorodithioates (U.S. Pat. No. 5,453,496) has also been described. Other non-phosphorous based modified polynucleotides can also be used (Stirchak et al. (1989) *Nucleic Acids Res.* 17:6129–6141). Polynucleotides with phosphorothioate backbones can be more immunogenic than those with phosphodiester backbones and appear to be more resistant to degradation after injection into the host. Braun et al. (1988) *J. Immunol.* 141:2084–2089; and Latimer et al. (1995) *Mol. Immunol.* 32:1057–1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2,3-d] pyrimidin-5-yl, 2-amino-4-oxopyrrolo [2.3-d] pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified polynucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an polynucleotide. Such base-modified nucleosides, present at either terminal or internal positions of an polynucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

The ISS used in the methods of the invention may be produced as ISS-microcarrier complexes. ISS-microcarrier complexes comprise an ISS-containing polynucleotide bound to a microcarrier (MC). ISS-MC complexes comprise an ISS bound to the surface of a microcarrier (i.e., the ISS is not encapsulated in the MC), adsorbed within a microcarrier (e.g., adsorbed to PLGA beads), or encapsulated within a MC (e.g., incorporated within liposomes).

ISS-containing oligonucleotides bound to microparticles (SEPHAROSE® beads) have previously been shown to have immunostimulatory activity in vitro (Liang et al., (1996), *J. Clin. Invest.* 98:1119–1129) However, recent results show that ISS-containing oligonucleotides bound to gold, latex and magnetic particles are not active in stimulating proliferation of 7TD1 cells, which proliferate in response to ISS-containing oligonucleotides (Manzel et al., (1999), *Antisense Nucl. Acid Drug Dev.* 9:459–464).

Microcarriers are not soluble in pure water, and are less than about 50–60 µm in size, preferably less than about 10 µm in size, more preferably from about 10 nm to about 10 µm, 25 nm to about 5 µm, 50 nm to about 4.5 µm or 1.0 µm to about 2.0 µm in size. Microcarrers may be any shape, such as spherical, ellipsoidal, rod-shaped, and the like, although spherical microcarriers are normally preferred. Preferred microcarriers have sizes of or about 50 nm, 200 nm, 1 µm, 1.2 µm, 1.4 µm, 1.5 µm, 1.6 µm, 1.8 µm, 2.0 µm, 2.5 µm or 4.5 µm. The "size" of a microcarier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5–10% of the stated measurement. Size characteristics may also be determined by dynamic light scattering. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

Microcarriers may be solid phase (e.g., polystyrene beads) or liquid phase (e.g., liposomes, micelles, or oil droplets in an oil and water emulsion). Liquid phase microcarriers include liposomes, micelles, oil droplets and other lipid or oil-based particles. One preferred liquid phase microcarrier is oil droplets within an oil-in-water emulsion. Preferably, oil-in-water emulsions used as microcarriers comprise biocompatible substituents such as squalene. Liquid phase microcarriers are normally considered nonbiodegradable, but may be biodegradable liquid phase microcarriers may be produced by incorporation of one or more biodegradable polymers in the liquid microcarrier formulation. In one preferred embodiment, the microcarrier is oil droplets in an oil-in-water emulsion prepared by emulsification of squalene, sorbitan trioleate, TWEEN 80® in an aqueous pH buffer.

Solid phase microcarriers for use in ISS-microcarrier complexes may be made from biodegradable materials or nonbiodegradable materials, and may include or exclude agarose or modified agarose microcarriers. Useful solid phase biodegradable microcarriers include, but are not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on sebacic acid, p-(carboxyphenoxy)propane, or p-(carboxyphenoxy)hexane; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al. (1996) *Biotechnol. Bioeng.* 1996:102); and polyamides such as poly(lactic acid-co-lysine). A wide variety of nonbiodegradable materials suitable for manufacturing microcarriers are also known, including, but not limited to polystyrene, polyethylene, latex, gold, and ferromagnetic or paramagnetic materials. Solid phase microcarriers may be covalently modified to incorporate one or more moieties for use in linking the ISS, for example by addition of amine groups for covalent linking using amine-reactive crosslinkers.

The ISS-microcarrier complexes may be covalently or non-covalently linked. Covalently linked ISS-MC complexes may be directly linked or be linked by a crosslinking moiety of one or more atoms (typically the residue of a crosslinking agent). The ISS may be modified to allow or augment binding to the MC (e.g., by incorporation of a free sulfhydryl for covalent crosslinking or addition of a hydrophobic moieties such as lipids, steroids, sterols such as cholesterol, and terpenes, for hydrophobic bonding), although unmodified ISS may be used for formation of non-covalent ISS-MC complex formation by electrostatic interaction or by base pairing (e.g., by base pairing at least one portion of the ISS with a complementary oligonucleotide bound to the microcarrier). ISS-containing polynucleotides may be linked to solid phase microcarriers or other chemical moieties to facilitate ISS-MC complex formation using conventional technology known in the art, such as use of available heterobifunctional crosslinkers (e.g., succinimidyl 4-(N-maleimidomethyl)cyclohexane-1-carboxylate or its sulfo-derivatives for covalently linking an amine-derivatized microcarrier and an ISS modified to contain a free sulfhydryl) or by addition of compounds such as cholesterol (e.g., by the method of Godard et al. (1995) *Eur. J. Biochem.* 232:404–410) to facilitate binding to hydrophobic microcarriers such as oil droplets in oil-in-water emulsions. Alternatively, modified nucleosides or nucleotides, such as are known in the art, can be incorporated at either terminus, or at internal positions in the ISS. These can contain blocked functional groups which, when deblocked, are reactive with a variety of functional groups which can be present on, or attached to, the microcarrier or a moiety which would facilitate binding to a microcarrier. Certain embodiments of noncovalently linked ISS-MC complexes utilize a binding pair (e.g., an antibody and its cognate antigen or biotin and streptavidin or avidin), where one member of the binding pair is bound to the ISS and the microcarrier is derivatized with the other member of the binding pair (e.g., a biotinylated ISS and a streptavidin-derivatized microcarrier may be combined to form a noncovalently linked ISS-MC complex).

Non-covalent ISS-MC complexes bound by electrostatic binding typically exploit the highly negative charge of the polynucleotide backbone. Accordingly, microcarriers for use in non-covalently bound ISS-MC complexes are generally positively charged (e.g., cationic) at physiological pH (e.g., about pH 6.8–7.4). The microcarrier may intrinsically possess a positive charge, but microcarriers made from compounds not normally possessing a positive charge may be derivatized or otherwise modified to become positively charged (e.g., cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles.

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vaccum, before storing at 4° C.

Generally, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

Physico-chemical characteristics such as mean size, size distribution and surface charge of dried microspheres may be determined. Size characteristics are determined, for example, by dynamic light scattering technique and the surface charge was determined by measuring the zeta potential.

Generally, ISS-containing polynucleotides can be adsorbed onto the cationic microspheres by overnight aqueous incubation of ISS and the particles at 4° C. Microspheres are characterized for size and surface charge before and after ISS association. Selected batches may then evaluated for activity as described herein.

Administration

An ISS-containing polynucleotide may be administered before, during and/or after exposure to a herpes virus. An ISS polynucleotide may also be administered before, during and/or after infection by a herpes virus. An ISS polynucleotide may also be administered before or after onset of symptoms of herpes virus infection. Accordingly, administration of ISS-containing polynucleotide may be at various times with respect to exposure to, infection by and/or onset of symptoms of infection by virus. Further, there may be one or more administrations. If the ISS-containing polynucleotide is administered on multiple occasions, the ISS may be administered on any schedule selected by the clinician, such as daily, every other day, every three days, every four days, every five days, every six days, weekly, biweekly, monthly or at ever longer intervals (which may or may not remain the same during the course of treatment). Where multiple administrations are given, the ISS-containing polynucleotide may be given in 2, 3, 4, 5, 6, 7, 8, 9, 10 or more separate administrations.

When ISS-containing polynucleotide is administered to an individual at risk of exposure to virus (i.e., before infection), ISS-containing polynucleotide is preferably administered less than about 14 days before exposure to virus, preferably less than about 10 days before exposure to virus, more preferably less than about 7 days before exposure to virus, even more preferably less than about 5 days before exposure to virus. In some embodiments, ISS-containing polynucleotide is administered about 3 days before exposure to virus.

In a further embodiment, the ISS-containing polynucleotide is administered after exposure to a herpes virus, but prior to appearance of symptoms. This embodiment is particularly relevant with respect to HSV-2 and VZV. Preferably, the ISS-containing polynucleotide is administered less than about three days after exposure, more preferably less than about one day, 12 hours, six hours or two hours after exposure, if the time of exposure is known or suspected.

In another embodiment, the ISS-containing polynucleotide is administered after appearance of at least one symptom of herpes virus infection. Preferably, ISS-containing polynucleotide is administered within about 28, 21, 14, 7, 5 or 3 days following appearance of a symptom of herpes virus infection. However, some infected individuals exhibiting symptoms will already have undertaken one or more courses of treatment with another therapy. In such individuals, or in individuals who failed to appreciate the import of their symptoms, the ISS-containing polynucleotide may be administered at any point following infection.

Additionally, treatments employing an ISS-containing polynucleotide may also be employed in conjunction with other treatments or as 'second line' treatments employed after failure of a 'first line' treatment. Treatments for herpes virus infection are known in the art.

ISS polynucleotides may be formulated in any form known in the art, such as dry powder, semi-solid or liquid formulations. For parenteral administration ISS polynucleotides preferably administered in a liquid formulation, although solid or semi-solid formulations may also be acceptable, particularly where the ISS polynucleotide is formulated in a slow release depot form. ISS polynucleotides are generally formulated in liquid or dry powder form for topical administration, although semi-solid formulations may be useful.

ISS polynucleotide formulations may contain additional components such as salts, buffers, bulking agents, osmolytes, antioxidants, detergents, surfactants and other pharmaceutically-acceptable excipients as are known in the art. Generally, liquid ISS polynucleotide formulations made in USP water for injection and are sterile, isotonic and pH buffered to a physiologically-acceptable pH, such as about pH 6.8 to 7.5.

ISS-containing polynucleotides may be formulated in delivery vehicles such as liposomes, oil/water emulsion or slow release depot formulations. Methods of formulating polynucleotides in such forms are well known in the art.

ISS-containing polynucleotide formulations may also include or exclude immunomodulatory agents such as adjuvants and immunostimulatory cytokines, which are well known in the art.

A suitable dosage range or effective amount is one that provides the desired reduction of symptoms and/or suppression of viral infection and depends on a number of factors, including the particular herpes virus, ISS sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for an ISS-containing polynucleotide of about 20 bases, a dosage range may be selected from, for example, an independently selected lower limit such as about 0.1, 0.25, 0.5, 1, 2, 5, 10, 20, 30 40, 50 60, 80, 100, 200, 300, 400 or 500 µg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 µg/kg. For example, a dose may be about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg, 500 to 1000 µg/kg, 500 to 5000 µg/kg, or 500 to 10,000 µg/kg. Generally, parenteral routes of administration require higher doses of ISS compared to more direct application to infected tissue, as do ISS-containing polynucleotides of increasing length.

Polynucleotides comprising an ISS may be administered by systemic (e.g., parenteral) or local (e.g., topical) administration.

In one embodiment, the ISS-containing polynucleotide(s) is topically administered. Topical administration may be at the site of infection (e.g. genital region in the case of HSV-2), it may be at a site of a symptom (e.g., a herpetic lesion) or it may be at the site of possible exposure to herpes virus (e.g., gential region).

In another embodiment, the ISS-containing polynucleotide(s) is injected locally into the area of lesion(s). Intralesional injection may be at the site of infection (e.g., genital region in the case HSV-2) or it may be at a site of a symptom (e.g., a herpetic lesion).

In other embodiments, the ISS-containing polynucleotide is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g. iontophoresis) or a combination thereof. A variety of devices are available for transdermal administration which may be used in accordance with the invention.

Nasopharyngeal and pulmonary routes of administration include, but are not limited to, intranasal, inhalation, transbronchial and transalveolar routes. The ISS-containing polynucleotide may thus be administered by inhalation of aerosols, atomized liquids or powders. Devices suitable for administration by inhalation of ISS-containing compositions include, but are not limited to, nebulizers, atomizers, vaporizers, and metered-dose inhalers. Nebulizers, atomizers, vaporizers and metered-dose inhalers filled with or employing reservoirs containing formulations comprising the ISS-containing polynucleotide(s) are among a variety of devices suitable for use in inhalation delivery of the ISS-containing polynucleotide(s). Other methods of delivering to respiratory mucosa include delivery of liquid formulations, such as by nose drops.

IV, IP, IM and ID administration may be by bolus or infusion administration. For SC administration, administration may be by bolus, infusion or by implantable device, such as an implantable minipump (e.g., osmotic or mechanical minipump) or slow release implant. The ISS polynucleotide(s) may also be delivered in a slow release formulation adapted for IV, IP, IM, ID or SC administration. Administration by inhalation is preferably accomplished in discrete doses (e.g., via a metered dose inhaler), although delivery similar to an infusion may be accomplished through use of a nebulizer. Administration via the transdermal and transmucosal routes may be continuous or pulsatile.

Assessment

In some embodiments, administration of an ISS-containing polynucleotide results in prevention, palliation, and/or improvement in one or more symptoms of herpes virus infection. The exact form of prevention, palliation or improvement will depend on the particular herpes virus, but includes reduction in size and/or duration of herpetic lesions (for all alphaherpesvirinae), reduction in symptoms of varicella (for VZV) or reduction in frequency or number of recurrent herpetic lesions (for all alphaherpesvirinae). In some embodiments, administration of an ISS-containing polynucleotide results in a reduction in viral titer (which indicates suppression of viral infection). In other embodiments, viral shedding (e.g., virus excretion) is reduced. In some embodiments, the level (e.g., magnitude or amount) of viral shedding is reduced. Viral shedding can occur with or without symptoms at the time of primary, initial or recurrent infection and may be detected, for example, by examination of tissue scrapings from suspected areas of infection for the presence of virus or virus nucleic acid. In other embodiments, viral infection is suppressed, which may be indicated by any one or more of a number of parameters, including, but not limited to, extent of one or more symptoms and viral titer. In other embodiments, recurrence, which is generally indicated by appearance of one or more symptoms associated with infection, is reduced.

Symptoms of infection may be assessed before and after administration of ISS-containing polynucleotide by the individual or the clinician. As will be apparent to one of skill in the art, the symptoms will vary depending on the particular herpes virus and the site of the symptoms. Symptoms of herpes simplex virus infection, which are well known in the art, include herpetic lesion, viral shedding, and, in some cases, neurovirulence. Symptoms of VZV infection include cutaneous and mucosal varicella lesions and fever and in recurrences, cutaneous lesions and neuropathy, particular of sensory nerves.

Viral titer may be assessed in biological samples using standard methods of the art. Levels of viral nucleic acid may be assessed by isolating nucleic acid from the sample and blot analysis using a viral polynucleotide sequence as a probe, or PCR analysis. Another method is to perform in situ hybridization with virus-specific probes. Other assays include biological measures such as quantitation of plaque forming units (PFU) or virus induced cytopathic effects (CPE), such as formation of syncytia. Extent or amount of viral particles may be measured from any infected area, such as infected tissue or mucosal discharge. When the sample is a liquid, viral titer is calculated in some indication of number or amount of virus or virus particles (e.g., infectious particles, plaque forming units, infectious doses, or median tissue culture infectious doses (TCID 50)) per unit volume. In solid samples, such as a tissue sample, viral titer is calculated in virus particles per unit weight. Reduction is indicated by comparing viral titer to viral titer measured at an earlier time point, and/or comparing to an estimated titer (based, for example, on animal or clinical studies) that represents untreated infection.

Kits of the Invention

The invention provides kits for carrying out the methods of the invention. Accordingly, a variety of kits are provided. The kits may be used for any one or more of the following (and, accordingly, may contain instructions for any one or more of the following uses): treating alphaherpesvirinae infection in an individual infected with alphaherpesvirinae; reducing viral shedding (including reducing the probability and/or risk of alphaherpesvirinae transmission); preventing alphaherpesvirinae infection in an individual at risk of being infected with alphaherpesvirinae; preventing alphaherpesvirinae infection in an individual who has been exposed to alphaherpesvirinae; preventing one or more symptoms of alphaherpesvirinae infection in an individual at risk of being exposed to alphaherpesvirinae; preventing one or more symptoms of alphaherpesvirinae infection in an individual who has been exposed to alphaherpesvirinae; reducing severity one or more symptoms of alphaherpesvirinae infection in an individual infected with alphaherpesvirinae; reducing recurrence of one or more symptoms of alphaherpesvirinae infection in an individual infected with alphaherpesvirinae; suppressing an alphaherpesvirinae infection in an individual infected with or at risk of being infected with alphaherpesvirinae; delaying development of an alphaherpesvirinae infection and/or a symptom of alphaherpesvirinae infection in an individual infected or at risk of being infected with alphaherpesvirinae; reducing duration of an alphaherpesvirinae infection in an individual infected or at risk of being infected with alphaherpesvirinae. As is understood in the art, any one or more of these uses would be included in instructions directed to treating or preventing alphaherpesvirinae infection.

The kits of the invention comprise one or more containers comprising an ISS-containing polynucleotide and a set of instructions, generally written instructions although electronic storage media (e.g., magnetic diskette or optical disk) containing instructions are also acceptable, relating to the use and dosage of the ISS-containing polynucleotide for the intended treatment (e.g., preventing one or more symptoms of alphaherpesvirinae infection in an individual at risk of being exposed to alphaherpesvirinae, preventing one or more symptoms of alphaherpesvirinae infection in an individual who has been exposed to alphaherpesvirinae, reducing severity of one or more symptoms of alphaherpesvirinae infection in an individual infected with alphaherpesvirinae, and/or reducing recurrence of one or more symptoms of alphaherpesvirinae infection in an individual infected with alphaherpesvirinae). The instructions included with the kit generally include information as to dosage, dosing schedule, and route of administration for the intended treatment. The containers of ISS may be unit doses, bulk packages (e.g., multi-dose packages) or sub-unit doses.

The kits of the invention do not include any packages or containers which contain viral antigens from the alphaherpesvirinae the kit is intended to to be used to treat. Accordingly, neither the container comprising the ISS-containing polynucleotide nor any other containers in the kit contain alphaherpesvirinae viral antigens.

The ISS component of the kit may be packaged in any convenient, appropriate packaging. For example, if the ISS is a freeze-dried formulation, an ampoule with a resilient stopper is normally used, so that the drug may be easily reconstituted by injecting fluid through the resilient stopper. Ampoules with non-resilient, removable closures (e.g., sealed glass) or resilient stoppers are most conveniently used for injectable forms of ISS. Also, prefilled syringes may be used when the kit is supplied with a liquid formulation of the ISS-containing polynucleotide. The kit may contain the ISS in an ointment for topical formulation in appropriate packaging. Also contemplated are packages for use in combination with a specific device, such as an inhaler, nasal administration device (e.g., an atomizer) or an infusion device such as a minipump.

As stated above, any ISS-containing polynucleotide described herein may be used, such as, for example, any polynucleotide comprising any of the following ISS: the sequence 5'-cytosine, guanine-3', the sequence 5'-T, C, G-3', the sequence 5'-C, G, pyrimidine, pyrimidine, C, G-3', the sequence 5'-purine, purine, C, G, pyrimidine, pyrimidine, C, G-3', the sequence 5'-purine, purine, C, G, pyrimidine, pyrimidine, C, C-3'; the sequence SEQ ID NO:1; the sequence SEQ ID NO: 9; the sequence 5'-purine, purine, B, G, pyrimidine, pyrimidine-3' wherein B is 5-bromocytosine or the sequence 5'-purine, purine, B, G, pyrimidine, pyrimidine, C, G-3' wherein B is 5-bromocytosine.

The following Examples are provided to illustrate, but not limit, the invention.

EXAMPLES

Example 1

Delay of HSV Disease Development in Mice by Administration of ISS

Outbred Swiss Webster mice, vaginally infected with HSV-2 strain 186, were used as a model of HSV infection. In these animals, the first indication of viral infection is hair loss and erythema (HLE) near the vagina occurring, on average, 5 days after inoculation. The next stage of infection is indicated by chronic wetness (CW) due to loss of bladder control, on average, 6 days after inoculation. A portion (about 50% of infected mice) of the animals develop hind limb paralysis (HLP) at approximately the same time point. Death, which is often preceded by evidence of CNS disease, occurs an average of 7–9 days after viral inoculation.

Mice were prepared for infection by an initial two-dose treatment with depopriven to synchronize cycles and to thin the vaginal epithelium. Vaginal mucous was removed by swabbing with calcium alginate, then a lethal challenge dose (determined by titration) of HSV-2 strain 186 was delivered by positive-displacement pipettor. Inoculated mice were randomly grouped into one of 4 treatment groups (n=15/group). Animals in group 1 received no treatment and served as a control for the study. Animals in the second and third groups were treated topically with 100 µg of an ISS-containing phosphorothioate oligonucleotide (5'-TGACTGTGAACGTTCGAGATGA-3') (SEQ ID NO:1) suspended in phosphate-buffered saline (PBS). The groups were treated 2 or 6 hours after inoculation. As a vehicle control, group four was treated with PBS alone.

Treatment with ISS resulted in decreased incidence (i.e., individuals showing symptoms of HSV-2 infection), improved survival and delays in both appearance of symptoms and time to death in symptomatic individuals. For those individuals which died during the experiment, average time to death was increased by an average of over two days in animals treated with ISS two hours after infection. Log rank analysis of the data indicated a statistical difference for both ISS treatment times compared to either the no treatment or PBS vehicle-treated groups (p=0.0014 and 0.0146, respectively). The data from this experiment are summarized in Table 1 (PI, post-inoculation).

TABLE 1

| Group | Incidence | Survival | Time to Symptoms | Time to Death |
|---|---|---|---|---|
| No Treatment | 15/15 (100%) | 0/15 (0%) | 4.73 d | 8.1 d |
| ISS 2h PI | 9/15 (60%) | 6/15 (40%) | 6.6 d | 12 d |
| ISS 6h PI | 12/15 (80%) | 4/15 (27%) | 5.75 d | 10.6 d |
| PBS 6h PI | 15/15 (100%) | 0/15 (0%) | 4.9 d | 9.5 d |

In another experiment, inoculated mice were randomly grouped into 8 treatment groups (n=16/group). Animals in the groups received treatments as outlined in Table 2 below. The groups were treated 2 hours after virus inoculation.

TABLE 2

| Group | Treatment |
|---|---|
| 1 | ISS; 5'-TGACTGTGAACGTTCGAGATGA-3' (SEQ ID NO:1) |
| 2 | ISS; 5'-TCGTCGAACGTTCGTTAACGTTCG-3' (SEQ ID NO:9) |
| 3 + 4 | non-ISS; 5'-TGACTGTGAAGGTTAGAGATGA-3' (SEQ ID NO:10) |
| 5 | non-ISS; 5'-TGACTGTGAACCTTAGAGATGA-3' (SEQ ID NO:11) |
| 6 | PBS |
| 7 | No Treatment |
| 8 | Acyclovir (ACV) |

In sum, treatment with ISS resulted in decreased incidence (i.e., individuals showing symptoms of HSV-2 infection), improved survival and delays in both appearance of symptoms and time to death in symptomatic individuals. For example, survival results of this experiment are depicted in FIG. 1. The survival curves for the animals treated with the two ISS oligonucleotides are indistinguishable from each other and are both significantly different from those of the groups treated with non-ISS oligonucleotides and PBS and the untreated group.

Example 2

Reduction of HSV Lesions in Guinea Pigs by Administration of ISS

Recurrent HSV-2 disease and aspects of the primary disease, including vesicular ulcerative lesion formation and asymptomatic shedding, are effectively modeled by inoculation of the guinea pig vagina with HSV-2 (Milligan et al. (1995) *Virol.* 206:234–241). In the guinea pig model, animals are infected by instillation of HSV-2 after calcium-alginate swabbing as described in Example 1. Three to five days after inoculation, cutaneous lesions develop and in some cases urinary retention is observed. The animals are scored daily for lesion severity using a 4 point scale (Bourne et al (1996) *J. Infect. Dis.* 173:800–807). Primary disease resolves by 14 days after inoculation (day 14 post-inoculation, d14 PI). From day 15 through 70 after inoculation, the animals are scored daily for the development of recurrent lesions. The frequency of recurrence is a significant outcome measure as it indicates any impact on latency and reactivation that a therapy may have. This model has proved to be a very effective system for testing of antivirals and vaccines (Bourne et al. (1996) *Vaccine* 14(13):1230–1234; Stanberry (1989) *Antiviral Res.* 11:203–214; Stanberry et al. (1990) *Antiviral Res.* 13:277–286).

Figure 2:
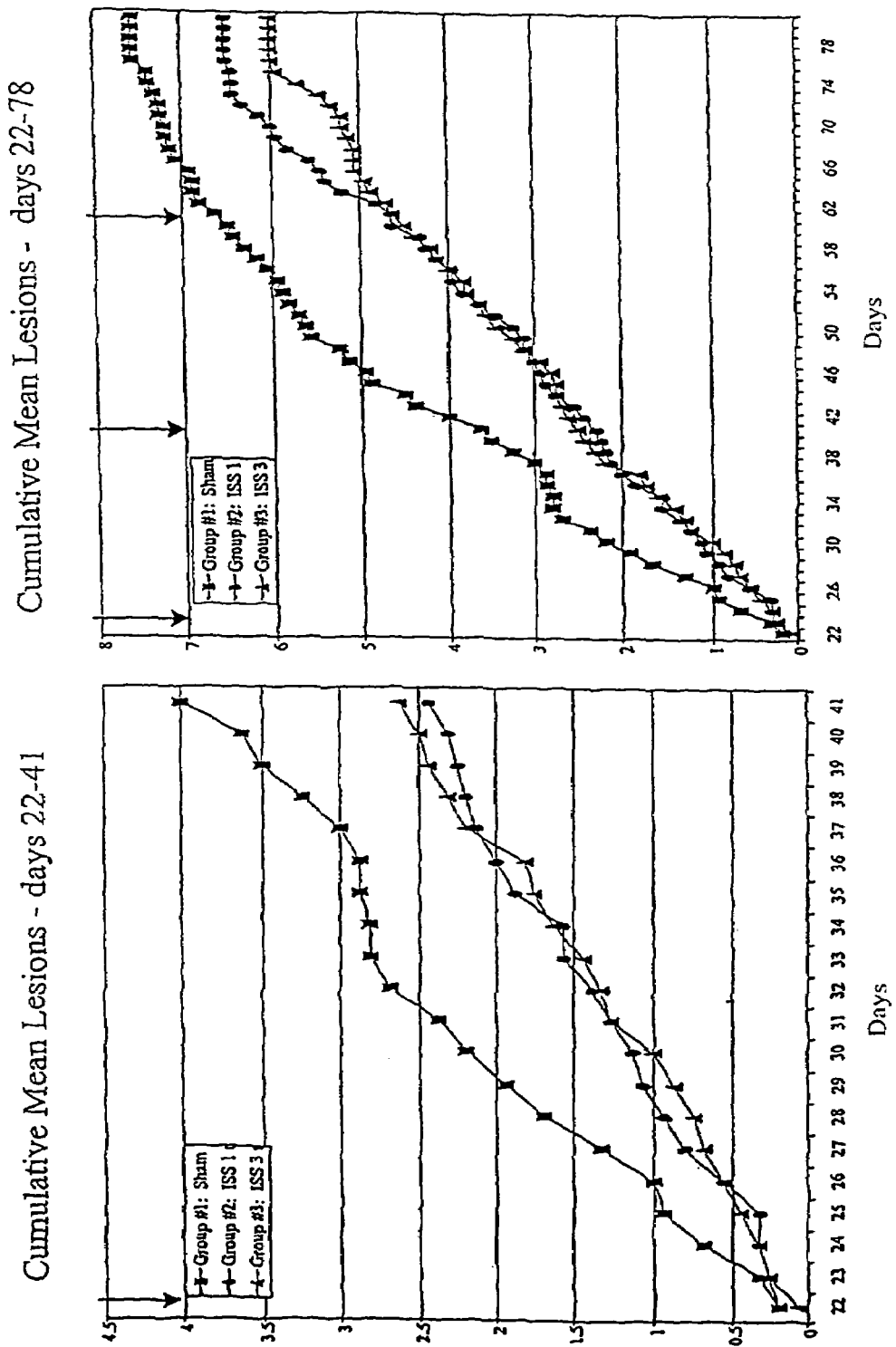
FIG. 2 summarizes results of ISS treatment of guinea pigs infected with HSV-2. The graphs depict cumulative mean herpetic lesions over the observation period in groups of animals receiving a single ISS treatment ("ISS 1"), receiving a total of three ISS treatments ("ISS 3") or receiving PBS alone ("sham").

Swiss Hartley guinea pigs (Charles River Laboratories) were intravaginally inoculated with HSV-2 strain MS by simply delivering virus to the vagina, then followed through the primary infection (d14 PI). Animals that did not display herpetic lesions were eliminated from further study. The remaining animals were randomly assigned to one of three study groups (n=16/group). To assess the impact of the ISS therapy upon recurrent lesion development, two of the three study groups were treated with 200 µg of the ISS-containing polynucleotide of Example 1 (5'-TGACTGTGAACGTTC-GAGATGA-3') (SEQ ID NO:1) suspended in PBS 21 days post inoculation. The third group received an injection of PBS alone. One of the two ISS treated groups received two additional ISS injections on days 42 and 63 post-inoculation (PI) (Group #3). Daily scoring of recurrent lesions was completed on each animal to determine the impact of ISS on recurrence frequency. These scores were averaged daily for each groups and the cumulative totals are depicted in FIG. 2. The graph on the left shows the period of time immediately following the first ISS injection (days 22–41), while the graph on the right shows the data over the entire observation period (day 22 through day 78).

Statistical analysis (ANOVA) of the results showed a significant reduction in the frequency of recurrences following ISS therapy (p=0.012). No difference was observed among the groups prior to ISS treatment. Although the results between multiple and single treatments were not statistically significant (p>0.05), data trends suggested that multiple treatments may further reduce recurrences.

In another experiment, guinea pigs were intravaginally inoculated with $5 \times 10^5$ pfu HSV-2, strain MS, as described above. The infected animals were divided into groups and received treatments as outlined in Table 3.

TABLE 3

| Group | Treatment |
|---|---|
| 1 | ISS; 5'-TGACTGTGAACGTTCGAGATGA-3' (SEQ ID NO:1); 1 mg in PBS; once at 21 days post inoculation |
| 2 | non-ISS; 5'-TGACTGTGAAGGTTAGAGATGA-3' (SEQ ID NO:10); 1 mg in PBS; once at 21 days post inoculation |
| 3 | No Treatment |
| 4 | Acyclovir (ACV); 3 times/day for 7 days starting at 6 hours post inoculation |

Figure 3:
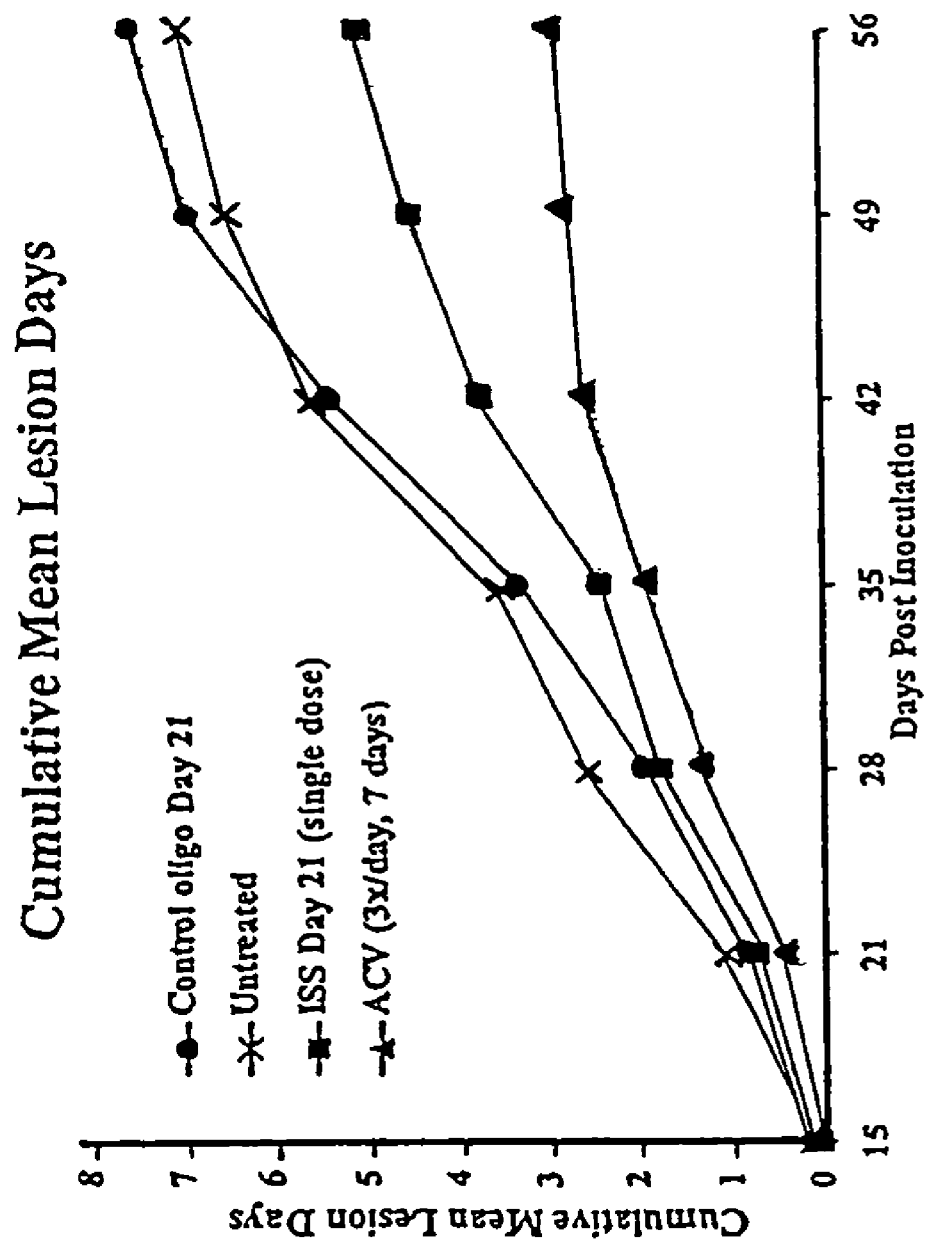
FIG. 3 summarizes results of ISS treatment of guinea pigs infected with HSV-2. The graph depicts cumulative mean herpetic lesions over the observation period in groups of animals receiving a single ISS treatment, a single non-ISS oligonucleotide treatment, 21 acyclovir treatments or no treatment.

Recurrent disease was monitored from day 15–56 post inoculation. Vaginal swabs of animals were done on days 21–43 and PCR analysis performed to determine the level of viral shedding. To evaluate the effect of ISS therapy on recurrent disease, cumulative number of recurrent lesions were monitored over time and the mean calculated for the group. Results from this experiment are depicted in FIG. 3. A single topical treatment with ISS at day 21 significantly decreased the cumulative mean recurrent lesion days compared to animals treated with non-ISS control oligonucleotide or untreated animals. The acyclovir (ACV) group also showed a significant reduction in cumulative recurrent mean lesion days, however this group received a total of 21 treatments spread over 7 days to achieve this effect.

Figure 4:
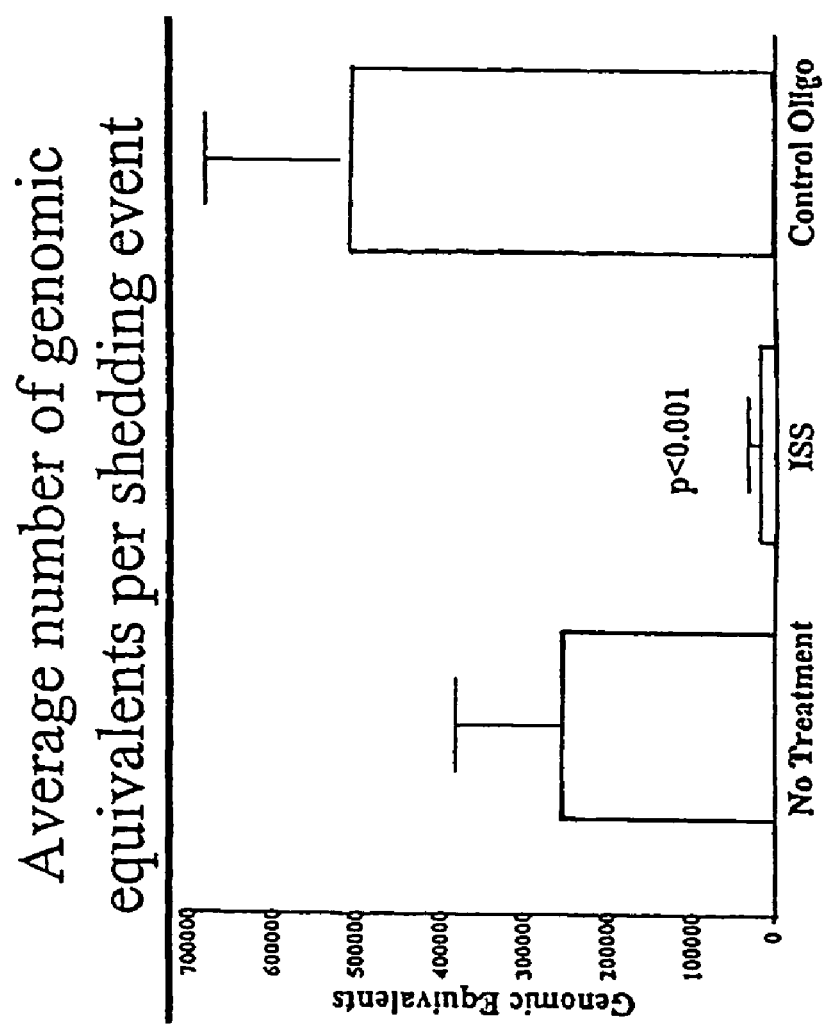
FIG. 4 is a graphical depiction of the average number of genomic equivalents per shedding event from herpetic lesions in guinea pigs.

The frequency of viral shedding was 20% of days for all groups. Thus, the frequency of viral shedding was unaffected by ISS treatment. However, as shown in FIG. 4, the magnitude of viral shedding was significantly reduced in the group receiving a single topical treatment with ISS as compared to the control groups. The p value ($p<0.001$) was calculated by ANOVA analysis using Dunn's Multiple Comparison test and is valid for both the untreated group and the non-ISS control oligonucleotide group. Magnitude of virus shedding is correlated with viral transmission. Since ISS treatment resulted in a reduction in the magnitude of viral shedding, ISS treatment may be effective in a reduction in viral transmission.

Example 3

ISS Demonstrates No Direct Activity on Viral Replication

As demonstrated in the following experiment, ISS appears to have no direct activity on viral replication.

Vero cells, a cell line derived from African Green monkey kidney, were pre-treated with varying concentrations of ISS or non-ISS oligonucleotides for varying times prior to the addition of HSV-1 or HSV-2. Oligonucleotides were used at 1 µg/ml or 10 µg/ml and the cells were incubated with the oligonucleotides for 30 seconds, 10 minutes or 24 hours. Viral titers were calculated as a percent of control titer generated by cells not treated with the oligonucleotides. The experimental conditions and results are summarized in Table 4 (NA=not available). The data are expressed as percent of control titer.

TABLE 4

| | 1 µg/ml | | | 10 µg/ml | | |
|---|---|---|---|---|---|---|
| Oligonucleotide | 30 sec | 10 min | 24 hr | 30 sec | 10 min | 24 hr |
| | Cells infected with HSV-1 | | | | | |
| SEQ ID NO:1 | 98 | 96 | 89 | 100 | 102 | 82 |
| SEQ ID NO:9 | 129 | 95 | 87 | 122 | 96 | 78 |
| SEQ ID NO:11 | 132 | 98 | 97 | 141 | 100 | 94 |
| SEQ ID NO:10 | 100 | 99 | 101 | 96 | 100 | 97 |
| | Cells infected with HSV-2 | | | | | |
| SEQ ID NO:1 | 101 | 98 | 99 | 101 | 101 | 99 |
| SEQ ID NO:9 | 119 | NA | NA | 136 | NA | NA |
| SEQ ID NO:11 | 111 | NA | NA | 129 | 100 | 98 |
| SEQ ID NO:10 | 98 | 96 | 103 | 103 | 97 | 99 |

HSV-1 or HSV-2 virus was pre-treated with varying concentrations of ISS or non-ISS oligonucleotides for 10 minutes prior to adding the mixture to plated Vero cells. Oligonucleotides were used at 1 µg/ml or 10 µg/ml. Viral titers were calculated as a percent of control titer generated by cells not treated with the oligonucleotides. The experimental conditions and results are summarized in Table 5. The data are expressed as percent of control titer.

TABLE 5

| | HSV-1 | | | HSV-2 | | |
|---|---|---|---|---|---|---|
| Oligonucleotide | 1 µg/ml | 10 µg/ml | control | 1 µg/ml | 10 µg/ml | control |
| SEQ ID NO:1 | 101 | 109 | 100 | 96 | 102 | 100 |
| SEQ ID NO:9 | 100 | 100 | 99 | 101 | 97 | 99 |
| SEQ ID NO:11 | 98 | 101 | 100 | 100 | 97 | 103 |
| SEQ ID NO:10 | 102 | 103 | 102 | 98 | 106 | 101 |

As shown in Tables 4 and 5, incubating the cells with ISS prior to HSV infection in vitro and incubating HSV virus with ISS prior to infecting cells in vitro has no effect on the viral titers from the infected cells as compared to controls.

The present invention has been detailed both by direct description and by example. Equivalents and modifications of the present invention will be apparent to those skilled in the art, and are encompassed within the scope of the invention.

What is claimed is:

1. A method for preventing a symptom of herpes simplex virus infection in an individual, comprising administering a composition comprising a polynucleotide comprising an immunostimulatory sequence (ISS) to an individual exposed to herpes simplex virus, wherein the ISS comprises the sequence 5'-C, G-3', wherein the polynucleotide comprises a phosphate backbone modification, wherein the polynucleotide is greater than 6 nucleotides and less than about 200 nucleotides in length, wherein a herpes simplex virus antigen is not administered in conjunction with administration of said composition, wherein the individual is a human and wherein said composition is administered after an exposure to herpes simplex virus and within three days after the herpes simplex virus exposure in an amount sufficient to prevent a symptom of herpes simplex virus infection.

2. The method of claim 1, wherein the ISS comprises the sequence 5'-T, C, G-3'.

3. The method of claim 1, wherein the ISS comprises the sequence 5'-purine, purine, C, G, pyrimidine, pyrimidine, C, G-3' or 5'-purine, purine, C, G, pyrimidine, pyrimidine, C, C-3'.

4. The method of claim 3, wherein the ISS comprises a sequence selected from the group consisting of 5'-AACGTTCC-3',5'-AACGTTCG-3', 5-GACGTTCC-3' and 5'-GACGTTCG-3'.

5. The method of claim 1, wherein the ISS comprises the sequence 5'-TGACTGTGAACGTTCGAGATGA-3' (SEQ ID NO:1).

6. The method of claim 1, wherein the ISS comprises the sequence 5'-TCGTCGAACGTTCGTTAACGTTCG-3' (SEQ ID NO:9).

7. The method of claim 1, wherein administration is at a site of infection.

8. The method of claim 1, wherein the herpes simplex virus is a herpes simplex virus 2 (HSV-2) virus.

9. A method of reducing severity of a symptom of herpes simplex virus infection in an individual, comprising administering a composition comprising a polynucleotide comprising an immunostimulatory sequence (ISS) to said individual, wherein the ISS comprises the sequence 5'-C, G-3' wherein the polynucleotide comprises a phosphate backbone modification, wherein the polynucleotide is greater than 6 nucleotides and less than about 200 nucleotides in length, wherein a herpes simplex virus antigen is not administered in conjunction with administration of said composition, wherein the individual is a human and wherein said composition is administered after an exposure to herpes simplex virus and within three days after the herpes simplex virus exposure in an amount sufficient to reduce severity of a symptom of herpes simplex virus infection.

10. The method of claim 9, wherein the ISS comprises a sequence selected from the group consisting of 5'-AACGTTCC-3', 5'-AACGTTCG-3', 5'-GACGTTCC-3' and 5'-GACGTTCG-3'.

11. The method of claim 9, wherein the ISS comprises the sequence 5'-TGACTGTGAACGTTCGAGATGA-3' (SEQ ID NO:1).

12. The method of claim 9, wherein the ISS comprises the sequence 5'-TCGTCGAACGTTCGTTAACGTTCG-7CG-3' (SEQ ID NO:9).

13. The method of claim 9, wherein the composition is administered in an amount sufficient to reduce the level of viral shedding.

14. The method of claim 9, wherein the herpes simplex virus is a herpes simplex virus 2 (HSV-2) virus.

15. A method of reducing recurrence of a symptom of a herpes simplex virus infection in an individual, comprising administering a composition comprising a polynucleotide comprising an immunostimulatory sequence (ISS) to said individual, wherein the ISS comprises the sequence 5-C, G-3', wherein the polynucleotide comprises a phosphate backbone modification, wherein the polynucleotide is greater than 6 nucleotides and less than about 200 nucleotides in length, wherein a herpes simplex virus antigen is not administered in conjunction with administration of said composition, wherein the individual is a human and wherein said composition is administered after an exposure to herpes simplex virus and within three days after the herpes simplex virus exposure in an amount sufficient to reduce recurrence of a symptom of herpes simplex virus infection.

16. The method of claim 15, wherein the ISS comprises a sequence selected from the group consisting of 5'-AACGTTCC-3', 5'-AACGTTCG-3', 5'-GACGTTCC-3' and 5'-GACGTTCG-3'.

17. The method of claim 15, wherein the ISS comprises the sequence
5'-TGACTGTGAACGTTCGAGATGA-3' (SEQ ID NO:1).

18. The method of claim 15, wherein the ISS comprises the sequence 5'-TCGTCGAACGTTCGTTAACGTTCG-3' (SEQ ID NO:9).

19. The method of claim 15, wherein the herpes simplex virus is a herpes simplex virus 2 (HSV-2) virus.

20. The method of claim 9, wherein the ISS comprises the sequence 5'-purine, purine, C, G, pyrimidine, pyrimidine, C, G-3' or 5'-purine, purine, C, G, pyrimidine, pyrimidine, C, C-3'.

21. The method of claim 15, wherein the ISS comprises the sequence 5'-purine, purine, C, G, pyrimidine, pyrimidine, C, G-3' or 5'-purine, purine, C, G, pyrimidine, pyrimidine, C, C-3'.

22. The method of claim 9 wherein said composition is parenterally administered.

23. The method of claim 15 wherein said composition is parenterally administered.

* * * * *

SEQUENCE LISTING

<160> NUMBER OF SEQ ID NOS: 11

<210> SEQ ID NO 1
<211> LENGTH: 22
<212> TYPE: DNA

```
<213> ORGANISM: Artificial Sequence
<220> FEATURE:
<223> OTHER INFORMATION: Polynucleotide containing CG

<400> SEQUENCE: 1
tgactgtgaa cgttcgagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgaccgtgaa cgttcgagat ga                                              22

<210> SEQ ID NO 3
<211> LENGTH: 23
<212> TYPE: DNA
<213> ORGANISM: Artificial Sequence
<220> FEATURE:
<223> OTHER INFORMATION: Polynucleotide containing CG

<400> SEQUENCE: 3
tcatctcgaa cgttccacag tca                                             23

<210> SEQ ID NO 4
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 4
tgactgtgaa cgttccagat ga                                              22

<210> SEQ ID NO 5
<211> LENGTH: 26
<212> TYPE: DNA
<213> ORGANISM: Artificial Sequence
<220> FEATURE:
<223> OTHER INFORMATION: Polynucleotide containing CG

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial Sequence
<220> FEATURE:
<223> OTHER INFORMATION: Polynucleotide containing (5-bromocytosine)G
<221> NAME/KEY: misc_feature
<222> LOCATION: (1)...(22)
<223> OTHER INFORMATION: n = 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: Polynucleotide containing (5-bromocytosine)G
<221> NAME/KEY: misc_feature
```

```
<222> LOCATION: (1)...(22)
<223> OTHER INFORMATION: n = 5-bromocytosine

<400> SEQUENCE: 7
tgactgtgaa ngttcgagat ga                                          22

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing (5-bromocytosine)G
<221> NAME/KEY: misc_feature
<222> LOCATION: (1)...(22)
<223> OTHER INFORMATION: n = 5-bromocytosine

<400> SEQUENCE: 8
tgactgtgaa ngttngagat ga                                          22

<210> SEQ ID NO 9
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 9
tcgtcgaacg ttcgttaacg ttcg                                        24

<210> SEQ ID NO 10
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 10
tgactgtgaa ggttagagat ga                                          22

<210> SEQ ID NO 11
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 11
tgactgtgaa ccttagagat ga                                          22
```